(12) United States Patent
Sun

(10) Patent No.: US 11,933,700 B2
(45) Date of Patent: Mar. 19, 2024

(54) ANALYTICAL SYSTEM COMPRISING SAMPLE MANAGEMENT MODULE AND METHOD THEREOF

(71) Applicant: Xiyuan Sun, Cleveland, OH (US)

(72) Inventor: Xiyuan Sun, Cleveland, OH (US)

(*) Notice: Subject to any disclaimer, the term of this patent is extended or adjusted under 35 U.S.C. 154(b) by 583 days.

(21) Appl. No.: 17/067,760

(22) Filed: Oct. 12, 2020

(65) Prior Publication Data

US 2022/0113224 A1    Apr. 14, 2022

(51) Int. Cl.
*B01L 3/00* (2006.01)
*B01L 3/02* (2006.01)
*G01N 1/14* (2006.01)
*G01N 33/558* (2006.01)
*G01N 33/574* (2006.01)
*G01N 1/00* (2006.01)

(52) U.S. Cl.
CPC .............. *G01N 1/14* (2013.01); *B01L 3/0293* (2013.01); *B01L 3/502* (2013.01); *B01L 3/563* (2013.01); *B01L 3/565* (2013.01); *G01N 33/558* (2013.01); *G01N 33/57419* (2013.01); *B01L 2300/042* (2013.01); *B01L 2300/0636* (2013.01); *B01L 2300/069* (2013.01); *B01L 2300/0848* (2013.01); *G01N 2001/002* (2013.01); *G01N 2001/1463* (2013.01)

(58) Field of Classification Search
None
See application file for complete search history.

(56) References Cited

U.S. PATENT DOCUMENTS

| | | | |
|---|---|---|---|
| 2009/0308185 A1* | 12/2009 | Wu | B01L 3/502 73/864.83 |
| 2019/0059860 A1* | 2/2019 | Shahaf | G01N 33/6893 |
| 2019/0187142 A1* | 6/2019 | Misner | G01N 33/54366 |

* cited by examiner

*Primary Examiner* — Rebecca M Giere
(74) *Attorney, Agent, or Firm* — George Guosheng Wang; Upstream Research and Patent LLC

(57) ABSTRACT

The present invention provides an analytical system comprising a sample management module. A pressure delivery assembly is configured to compress and deform a mixing chamber containing a sample preparation, and simultaneously open a plug of the mixing chamber to release the sample preparation. The system can be manufactured as a sample box combinable to a detector box, and is particularly convenient for patients to use at home, for example, screening colorectal cancer with their fecal sample.

20 Claims, 39 Drawing Sheets

ANALYTICAL SYSTEM COMPRISING SAMPLE MANAGEMENT MODULE AND METHOD THEREOF

CROSS-REFERENCE TO RELATED APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

FIELD OF THE INVENTION

The present invention generally relates to an analytical system comprising sample management module, and methods thereof. Although the invention will be illustrated, explained and exemplified by a household device useful in the cancerology field, such as sampling a fecal sample of the user and in vitro diagnosing or screening colorectal cancer, it should be appreciated that the present invention can also be implemented as e.g. an analytical system in a laboratory that is useful in other fields, for sampling/aliquoting any sample, and detecting and measuring any analyte of interest in the sample.

BACKGROUND OF THE INVENTION

The large intestine is an organ that stores residual bowel contents after digestion and absorption, and produces feces while absorbing water. The large intestine begins with the cecum, which is then connected to the ascending colon, the transverse colon, the descending colon, the sigmoid colon, the rectum, and the anal canal.

Colorectal cancer (CRC) is commonly also known as colon cancer or a bowel cancer, and is one of the most frequently diagnosed malignancies and a leading cause of cancer-related deaths worldwide. Colorectal cancer is a cancer from uncontrolled cell growth in the colon or rectum (parts of the large intestine), or in the appendix. Symptoms typically include rectal bleeding and anemia which are sometimes associated with weight loss and changes in bowel habits. Most colorectal cancer occurs due to lifestyle and increasing age, with only a minority of cases associated with underlying genetic disorders. It typically starts in the lining of the bowel, and if left untreated, can grow into the muscle layers underneath, and then through the bowel wall.

High degree of mortality associated with CRC is largely due to late disease detection. Like in many cancers, the CRC patient's survival time depends on disease development stage. Patients with early stages (Stage 0, I and II) have good prognosis (more than 75%). Stages III have a more heterogeneous survival rate (from 90% down to 50%) depending on the tumor invasion on peripheral tissues. Finally, only stage IV is showing a fast and significant effect on the patient survival time: Only about 10% of patients are surviving more than 60 months after diagnosis.

Early detection, and surgery with excision of the tumor, is normally of critical importance for successful CRC treatment. Unfortunately, colorectal tumors have often grown to a considerable size before detection, and metastases are not uncommon. The tumor typically metastasizes to regional lymph nodes, but distant metastasis to the liver and lung are also common.

Colorectal cancer starts with a precancerous polyp (abnormal growth) in the colon, which can be found by early detection approaches. Colorectal cancer and its precancerous polyps have a tendency to bleed and mixed into the feces. Fecal occult blood (FOB) test looks for tiny traces of blood in the feces and can be used for early detection of CRC. There are two types of FOB approaches that have been recommended for non-invasive CRC detection, guaiac fecal occult blood test (gFOB), and Fecal Immunochemical Testing (FIT).

The guaiac-based tests measure the heme (non-protein) part of hemoglobin from blood in the feces, but they may be interfered by some types of food intake. As such, dietary restrictions are required for the patients before testing. The FIT tests are designed to detect hemoglobin by specific antibodies, so no dietary restriction is required prior to testing. FITs are therefore promising as an easy-to-perform and well-tolerated primary care based investigation for CRC screening. These important features made FIT superior to gFOB, despite that false-negative result from FIT in colorectal cancer screening cannot be avoided, especially in detecting lesions in the distal part of the colon. The degradation of hemoglobin (Hb) by fecal enterobacteria during longer intestinal retention was one of the causes of the false-negative results. Transferrin (TO is an iron-transporting protein that is present in normal blood. Tf is highly stable and more sensitive which could be considered as an indicator of bleeding to assist Hb.

There are also two kinds of FITs, qualitative FIT and quantitative FIT. The qualitative FIT is easy-to-perform but it lacks accuracy. A proliferation of point-of-care qualitative FITs have emerged for use in a clinical settings or at home. These FITs could be used to address test-related barriers by improving acceptability and diagnostic accuracy, but most of these tests are qualitative FIT, and they are not very sensitive for asymptomatic patients.

For quantitative FITs, the detection thresholds can be selected for individual populations with automated interpretation which allows for standardization and less inter-observer variations. With lowering the positive FIT cut-off, more malignancies may be detected. But quantitative FITs mostly rely on laboratory based equipment and professional operation. Therefore, quantitative, sensitive, and user-friendly FITs are needed.

Advantageously, the present invention provides a solution to meet the need. The system of the invention is highly efficient and easy to use for both home users and laboratory technicians. With the invented analytical system, the sampling a fecal sample of the user as well as the diagnosing or screening of colorectal cancer at home is accurate and fast. For example, the present invention provides a household device that is very easy and convenient to use at home. The method of the invention is less tedious and messy, and it can limit, or even eliminate, the risk of compromising or contaminating the sample during collection, transport, and testing.

SUMMARY OF THE INVENTION

One aspect of the present invention provides an analytical system comprising a sample collection module, a sample management module, and a sample analysis module. The sample management module includes a mixing chamber, a sample tray, and a pressure delivery assembly. The mixing chamber is configured for receiving an amount of sample from the sample collection module and also for mixing the received sample with a liquid such as a sample preservation fluid to formulate a sample preparation. The mixing chamber includes an outlet opening for releasing the sample preparation from the mixing chamber. The sample tray is located below the mixing chamber, and it has a raised and enclosed rim to define a receptacle area for receiving an amount of the sample preparation released from the mixing chamber. An island is protruded out from the receptacle area, and it engages with (or plugs into) the outlet opening of the mixing chamber and seals the outlet opening to prevent releasing of the sample preparation through it. The pressure delivery assembly includes a lower member below the sample tray and an upper member above the sample tray. The upper member is configured for contacting against the mixing chamber. The lower member is contactable to the upper member. When the analytical system is in use, a force from the lower member can be exerted up against the upper member which transmits the force along against the mixing chamber so as to squeeze/compress and deform the mixing chamber, reduce a volume thereof, and in the meanwhile, disengage the outlet opening from the island to unseal (or unplug) the outlet opening, and release an amount of the sample preparation from the mixing chamber into the receptacle area. The sample preparation released into the receptacle area is then delivered to the sample analysis module.

Another aspect of the invention provides an analytical method of using the analytical system as described above. The method include the following steps:

(1) collecting a sample or a specimen such as, but not limited to, fecal or other biological matter (hereinafter collectively "sample") with the sample collection module;
(2) aliquoting the sample and mixing the aliquoted sample with a liquid such as a sample preservation fluid to formulate a sample preparation in the mixing chamber;
(3) applying a force up against the upper member with the lower member and transmitting the force against the mixing chamber;
(4) squeezing/compressing and deforming the mixing chamber to reduce a volume thereof, and simultaneously disengaging the outlet opening from the island to unseal (or unplug) the outlet opening;
(5) releasing an amount of the sample preparation from the mixing chamber into the receptacle area; and
(6) analyzing the released sample preparation with the sample analysis module.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

It is also to be understood that the terminology used herein is for the purpose of describing particular embodiments only, and is not intended to limit the scope of the invention. For example, when an element is referred to as being "on", "connected to", or "coupled to" another element, it can be directly on, connected or coupled to the other element or intervening elements may be present. In contrast, when an element is referred to as being "directly on", "directly connected to", or "directly coupled to" another element, there are no intervening elements present.

Throughout the specification and claims, the following terms take the meanings explicitly associated herein, unless the context clearly dictates otherwise. The phrase "in one embodiment" does not necessarily refer to the same embodiment, although it may. Furthermore, the phrase "in another embodiment" does not necessarily refer to a different embodiment, although it may. Thus, as described below, various embodiments of the invention may be readily combined without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

A sample or a specimen in the present invention may include, but not limited to, fecal or other biological and non-biological matter (hereinafter collectively "sample"). In addition to stools, biological samples may also include biological fluids such as whole blood or derivatives thereof, for example serum or plasma, urine, saliva and effusions, bone marrow, and cells purified from these liquid samples.

Figure 1:
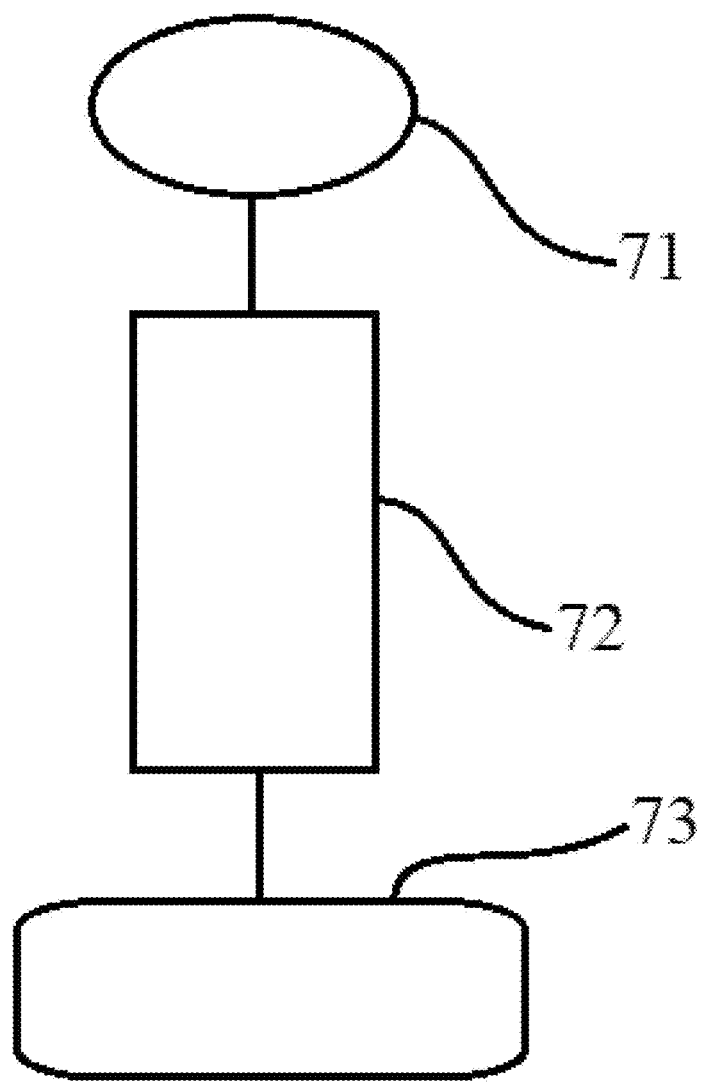
FIG. 1 schematically shows an analytical system in accordance with an exemplary embodiment of the present invention.

With reference to FIG. 1, an analytical system 70 includes a sample collection module 71, a sample management module 72, and a sample analysis module 73. A sample will be collected with the sample collection module 71, transferred to the sample management module 72 for sample processing, and then delivered to the sample analysis module 73 for analysis.

Figure 2:
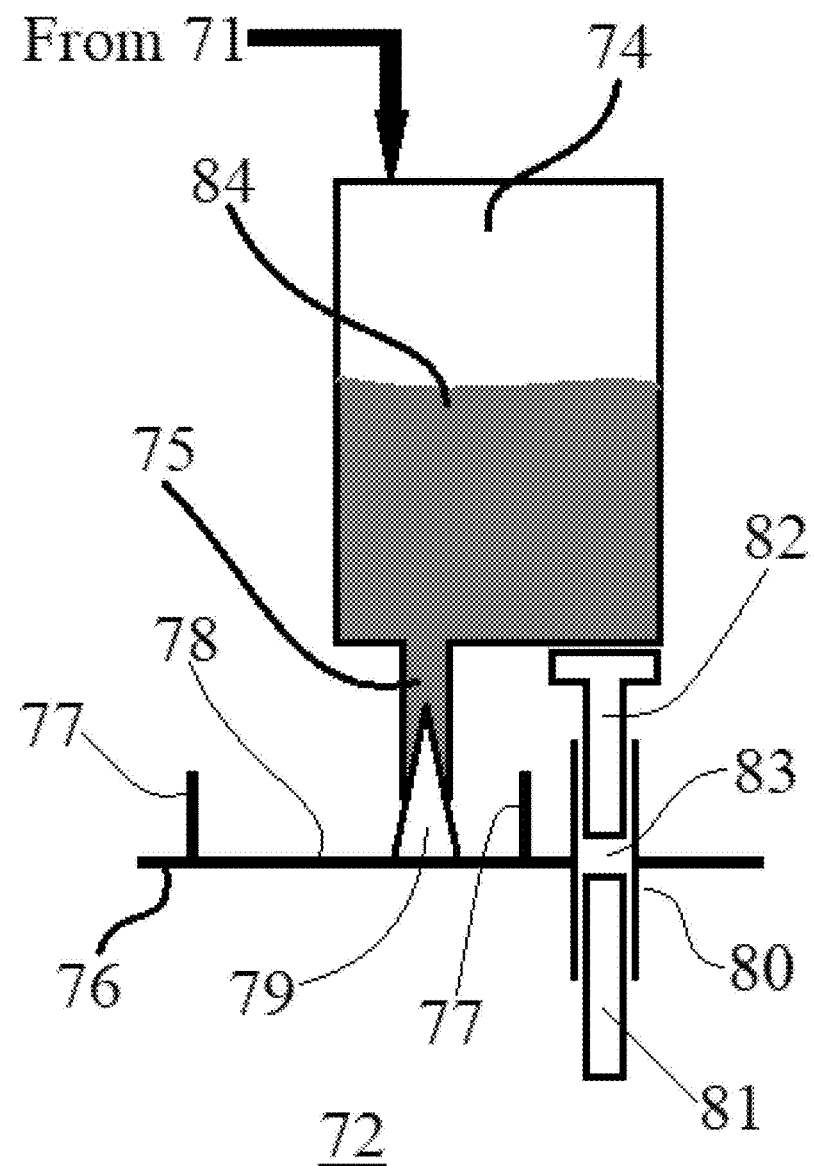
FIG. 2 illustrates a sample management module in a closed configuration before releasing a sample to the sample analysis module in accordance with an exemplary embodiment of the present invention.

Referring to FIG. 2, the sample management module 72 includes a mixing chamber 74, a sample tray 76, and a pressure (or force) delivery assembly 80. The mixing chamber 74 receives an amount of sample to be tested from the sample collection module 71. The received sample is then mixed with a liquid such as a sample preservation fluid in the mixing chamber 74 to formulate a sample preparation 84. An outlet opening 75 is configured for releasing the sample preparation 84 from the mixing chamber 74.

Referring again to FIG. 2, the sample tray 76 may be located below the mixing chamber 74. A receptacle area 78 of the sample tray 76 is formed by a raised and enclosed rim 77, and is configured for receiving an amount of the sample preparation 84 released from the mixing chamber 74. An island 79 is protruded out (upward) from the receptacle area 78. Before releasing the sample preparation 84, the island 79 engages with (or plugs into) the outlet opening 75 of the mixing chamber 74 and seals the outlet opening 75 to prevent releasing of the sample preparation 84 through it. The pressure/force delivery assembly 80 may include a lower member 81 below the sample tray 76 and an upper member 82 above the sample tray 76. The upper member 82 is configured for contacting against the mixing chamber 74, and the lower member 81 is contactable to, or configured to contact, the upper member 82.

Figure 3:
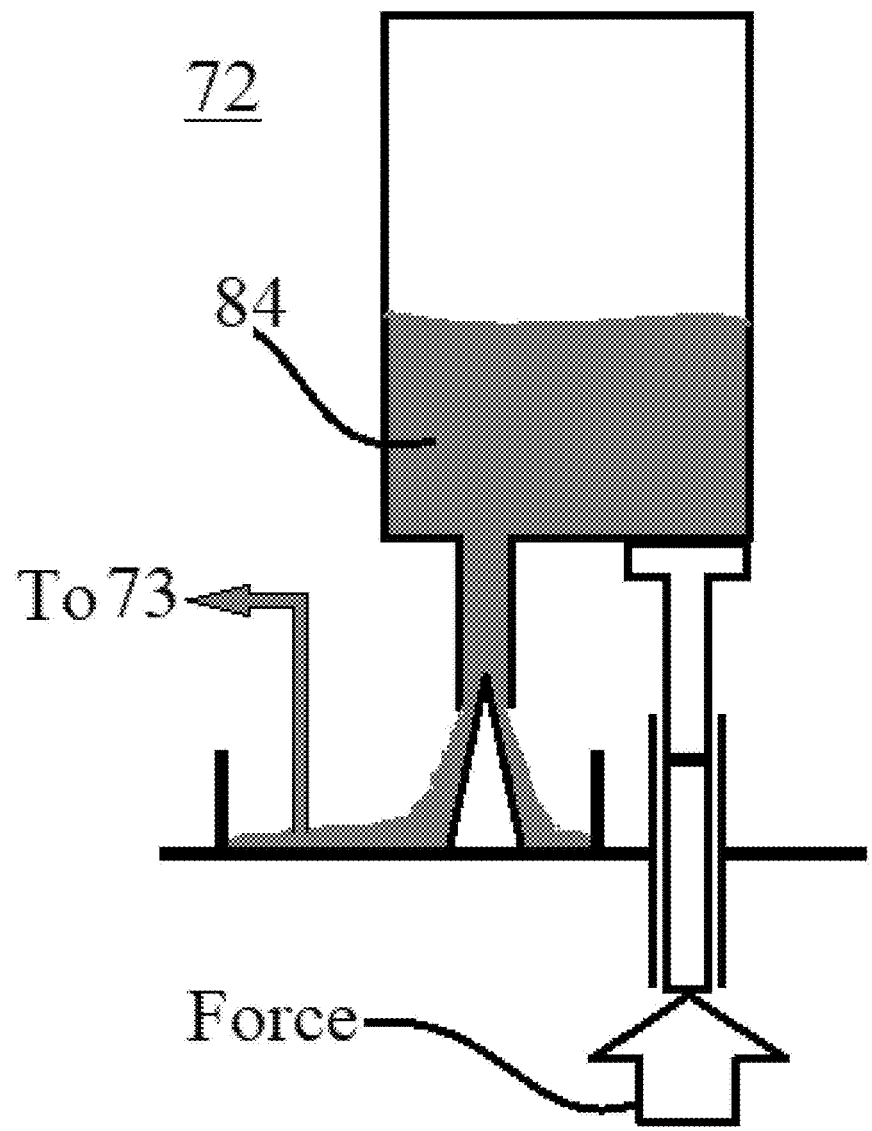
FIG. 3 illustrates a sample management module in an open configuration for releasing a sample to the sample analysis module in accordance with an exemplary embodiment of the present invention.

As shown in FIG. 3, when releasing the sample preparation 84, a force from the lower member 81 can be exerted (or applied) up against the upper member 82 which transmits the force along against the mixing chamber 74. The force may then squeeze/compress and deform the mixing chamber 74, reduce a volume thereof, and in the meanwhile, disengage the outlet opening 75 from the island 79 to unseal (or unplug) the outlet opening 75. The internal space ("head space") of the mixing chamber 74 above the sample preparation 84 is configured to be substantially airtight. Therefore, a predetermined amount of the sample preparation 84 is then released from the mixing chamber 74 into the receptacle area 78. The term "force" herein should be appreciated in the context of the third of Newton's laws of motion of classical mechanics, all forces occur in pairs such that if one object exerts an action force on another object, then the second object exerts an equal and opposite reaction force on the first. The force can be an action force and/or an opposite reaction force applied between the mixing chamber 74, the upper member 82, and the lower member 81. The sample preparation 84 released into the receptacle area 78 may then be delivered to the sample analysis module 73 for analysis.

Figure 4:
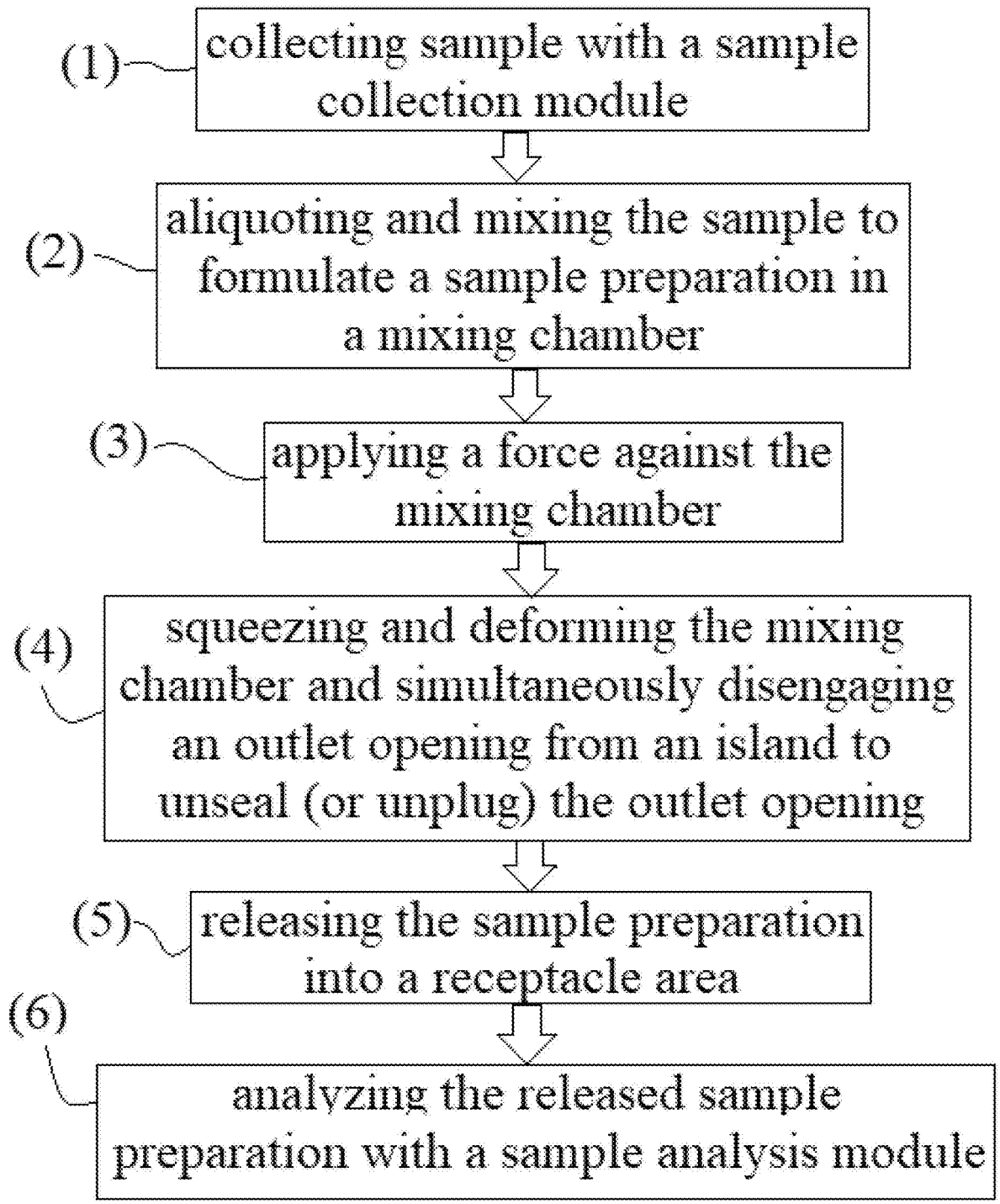
FIG. 4 demonstrates an analytical method of using the analytical system in accordance with an exemplary embodiment of the present invention.

With reference to FIG. 4, the present invention provides a method of using the analytical system as illustrated in FIGS. 1-3 and described above. As illustrated in FIGS. 1-4, the method may include the following steps:

(1) collecting a sample with the sample collection module 71;

(2) aliquoting the sample and mixing the aliquoted sample with a liquid such as a sample preservation fluid to formulate a sample preparation 84 in the mixing chamber 74;

(3) applying a force up against the upper member 82 with the lower member 81 and transmitting the force against the mixing chamber 74;

(4) squeezing/compressing and deforming the mixing chamber 74 to reduce a volume thereof, and simultaneously disengaging the outlet opening 75 from the island 79 to unseal (or unplug) the outlet opening 75;

(5) releasing an amount of the sample preparation 84 from the mixing chamber 74 into the receptacle area 78; and (6) analyzing the released sample preparation 84 with the sample analysis module 73.

Referring back to FIGS. 2-3, in preferred but still exemplary embodiments, the pressure delivery assembly 80 may further include an alignment channel 83 to align the movement of the lower member 81 and the movement of the upper member 82, before the two members (81, 82) meet and contact each other. Preferably, the sample tray 76 and the alignment channel 83 are structurally integrated to each other, e.g., the two may be molded together and chemically manufactured as a single piece.

Figure 5:
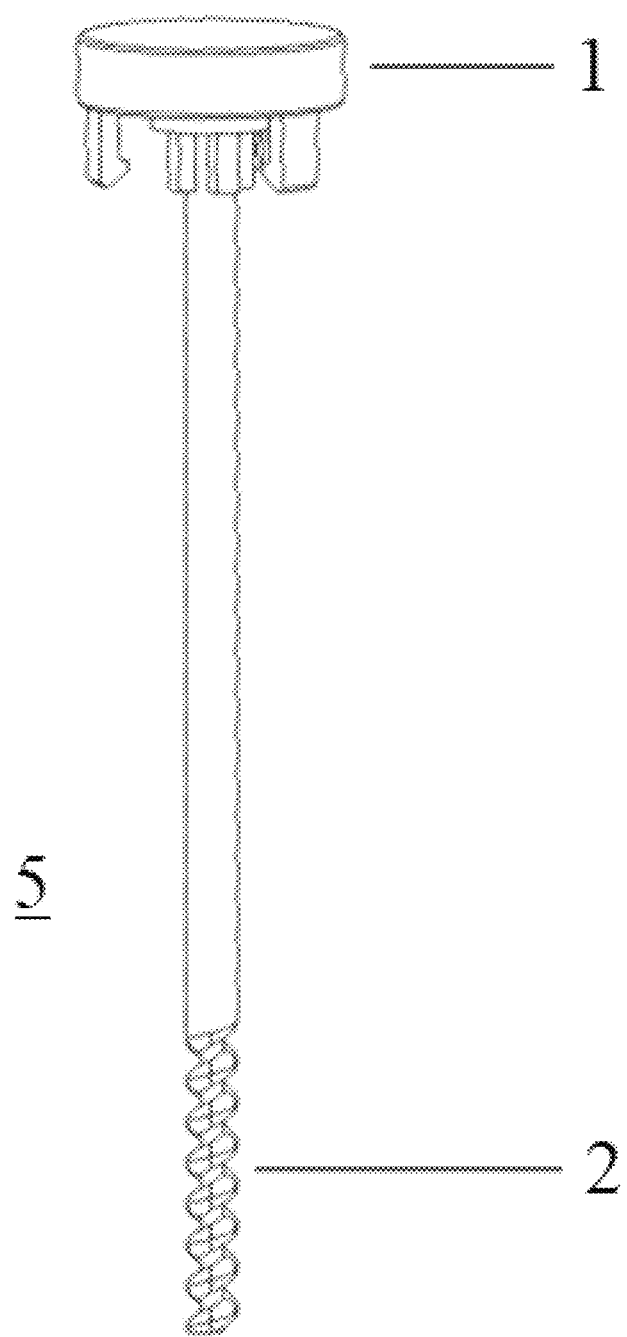
FIG. 5 depicts a sample collection rod in accordance with an exemplary embodiment of the present invention.

With reference to FIG. 5, an exemplary embodiment of the sample collection module 71 may include a sample collection rod 5 with a locking cap 1 on one end (proximal to the user), and grooves or trenches on its shaft surface, such as spiral grooves 2. The grooves can be filled or loaded with the raw sample of interest. Preferably, the full volume (or loading capacity) of the grooves or trenches 2 is predetermined, and the full volume will determine the amount of the raw sample of interest (i.e. an aliquoted amount of the raw sample) carried by the grooves or trenches 2 and delivered into the mixing chamber 74.

Figure 6:
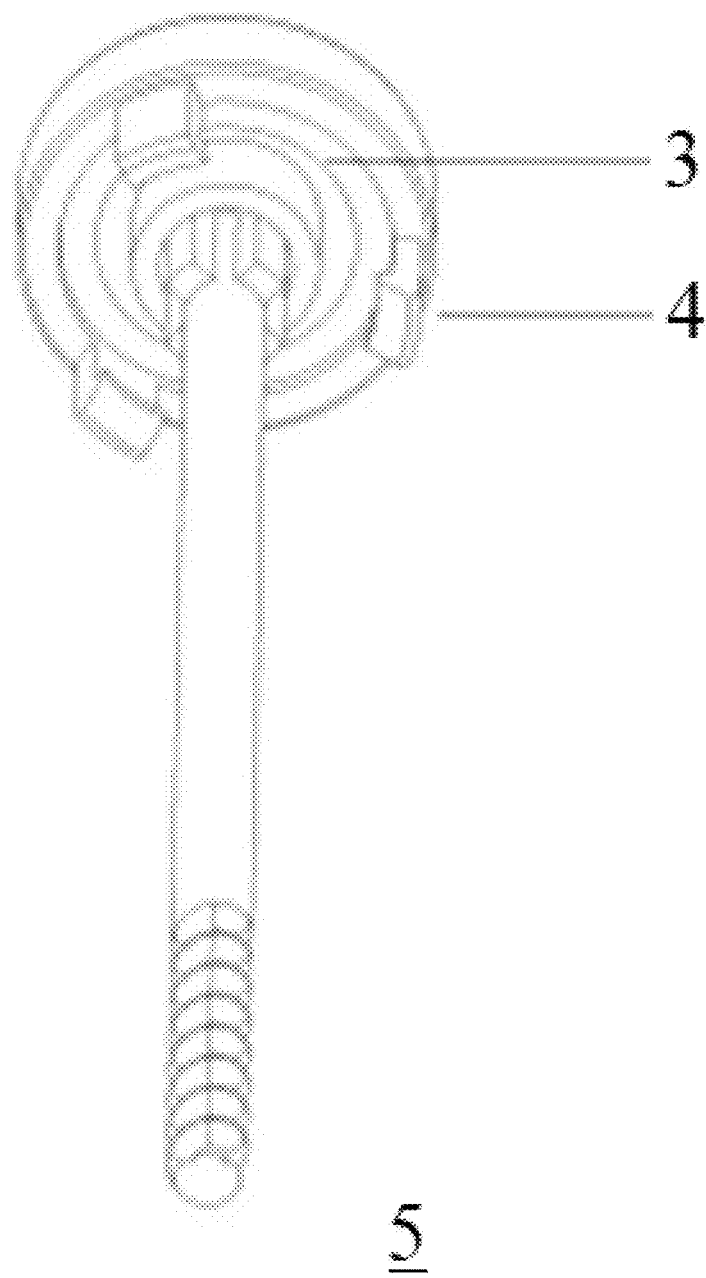
FIG. 6 is a perspective view of the sample collection rod in accordance with an exemplary embodiment of the present invention.
Figure 7:
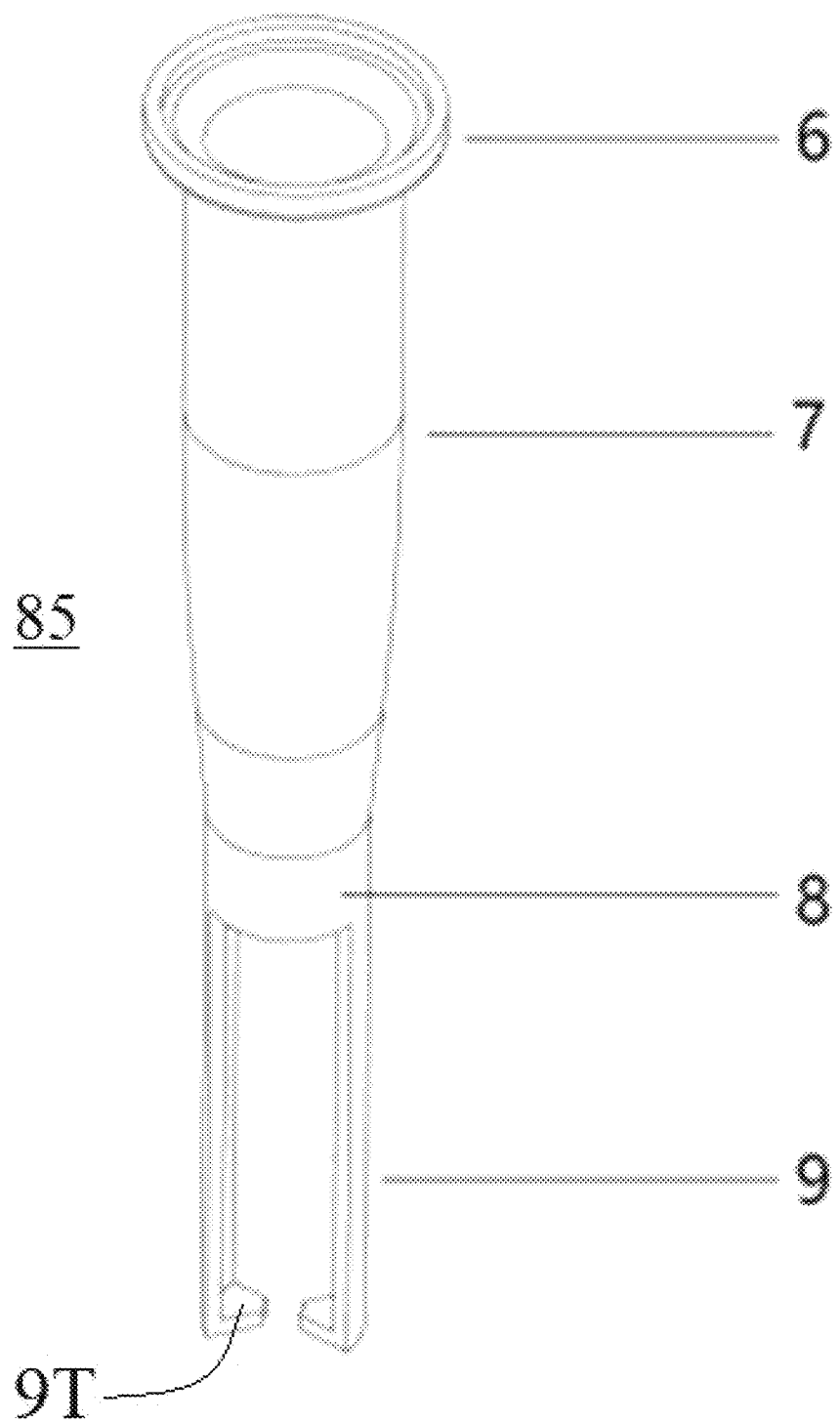
FIG. 7 shows a sample funnel in accordance with an exemplary embodiment of the present invention.

With reference to FIG. 6, the locking cap 1 of the sample collection rod 5 may include an attaching or fastening structure 4 configured to lock and seal the top opening 6 of a funnel 85 (as shown in FIG. 7, which will be described in more details). The locking cap 1 may preferably include a mechanical seal such as gasket 3 that fills the space between a mating surface on the locking cap 1 and another mating surface on the top opening 6 of the funnel 85, to prevent air leakage from the mixing chamber 74, when the mixing chamber 74 is being compressed or squeezed. The attaching or fastening structure 4 in FIG. 6 may be a cantilever snap-fit, with a design for multiple uses or single use (i.e. permanent snap-fit). A multiple use snap-fit usually has a lever or pin to be pushed, in order to undo the snap-fit. However, on a permanent snap-fit there is no lever or pin. Attempting to undo a permanent snap-fit can result in the piece breaking. It should be appreciated that the locking cap 1 may be secured to the top opening 6 of the funnel 85 with any other attaching or fastening structures, such as a threaded connection, and a bayonet attachment, in any suitable matter such as a friction fit, interference fit, snap fit, fasteners, clips, and the like. For example, threads may be formed about the top opening 6 of the funnel 85 and complimentary threads may be formed within the locking cap 1 so that the locking cap 1 may be threadably attached to and detached from the top opening 6 of the funnel 85.

With reference to FIG. 7, the sample management module 72 may include a sample funnel 85 for the sample collection rod 5 loaded with a collected sample to go through within. The funnel 85 has a top opening 6, and a bottom opening 8 that is smaller than the top opening 6. The internal diameter of the bottom opening 8 is not bigger than (equal to or slightly smaller than) the external diameter of the sample collection rod 5. The bottom opening 8 is so configured that, when the sample collection rod 5 goes through the bottom opening 8, all the sample collected on the sample collection rod 5 except the sample within (i.e. filled into or aliquoted in) the spiral grooves 2 are wiped off from the rod, and are prevented from mixing with the liquid such as a sample preservation fluid in the mixing chamber 74 to formulate the sample preparation 84. In other words, sample "overflow" from the spiral grooves 2 (or "extra sample") is wiped off from the rod 5 and trapped in the funnel 85 above bottom opening 8. There is a middle portion 7 of the funnel 85 between the top opening 6 and the bottom opening 8, which will be described in more details later.

In preferred embodiments, the funnel 85 further comprises one, two or more fingers 9 extended from a peripheral of the bottom opening 8. The tip(s) 9T of the fingers 9 is (are) configured to contact the sample collection rod 5, and to remove (or shake off, or wipe off, or scratch off, or unload/release) the sample within the spiral grooves 2 from the sample collection rod 5, when the rod 5 is moving downward. Preferably, the tip(s) 9T of the one, two or more fingers 9 is (are) bended inwardly (i.e. toward the sample collection rod 5). In one embodiment, clipping tips 9T are connected at the bottom of the funnel 85 to scrape out the fecal sample from the spiral grooves 2, when the grooves passes between the clipping tips.

Figure 8:
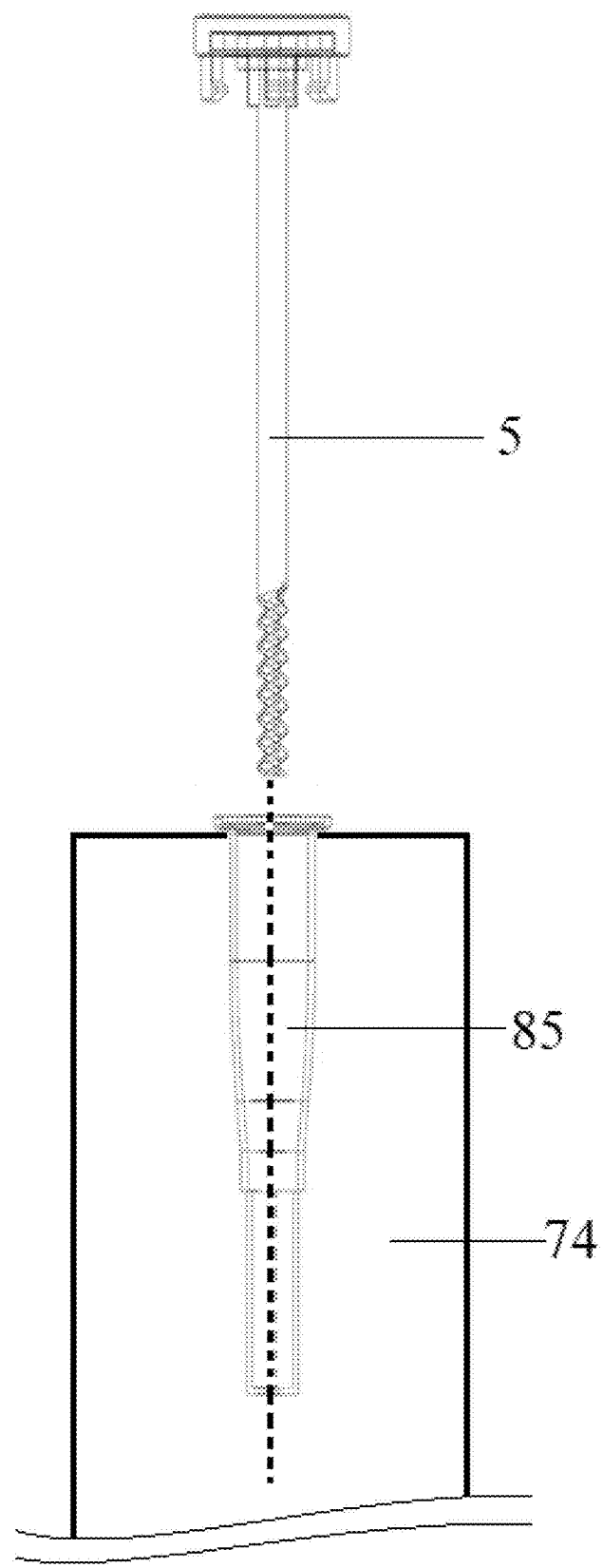
FIG. 8 schematically shows a sample collection rod inserting into a sample funnel in accordance with an exemplary embodiment of the present invention.

The locking cap 1 of the sample collection rod 5 may be configured to lock and seal the top opening 6 of the funnel 85, after the sample collection rod 5 is inserted all the way (or snapped) into the funnel 85 and the mixing chamber 74, as shown in FIG. 8.

Figure 9:
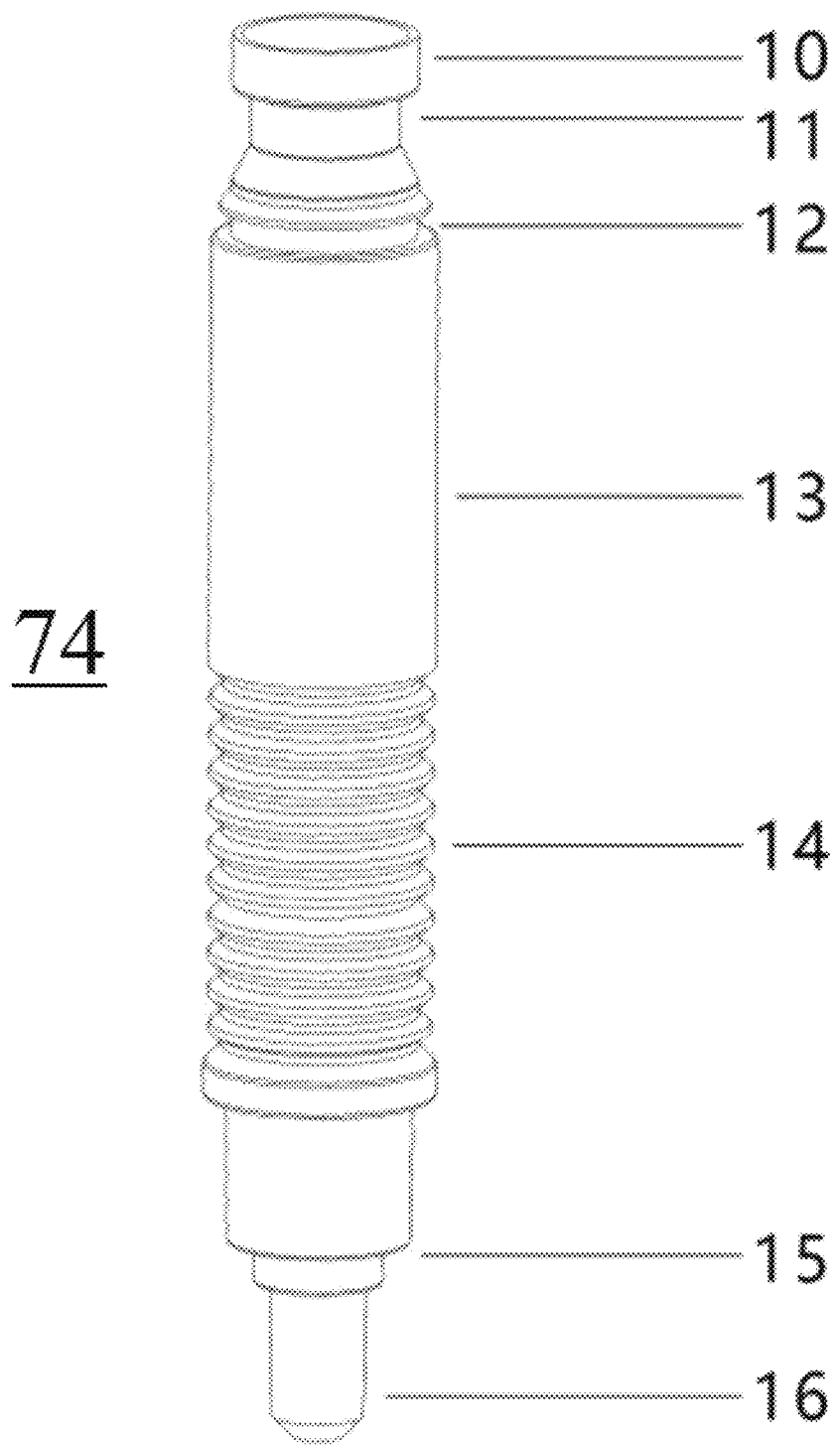
FIG. 9 demonstrates a mixing chamber in accordance with an exemplary embodiment of the present invention.

With reference to FIG. 9, the mixing chamber 74 may have a tubular structure made of any suitable material such as polypropylene (PP). The middle portion of the tubular structure may include a corrugated segment 14 and a non-corrugated (or flat) segment 13. The lower portion of the mixing chamber 74 may include an outlet opening 16, as an embodiment of the outlet opening 75 in FIGS. 2-3; and a contacting shoulder 15 (e.g. facing down) for receiving a force or pressure from the upper member 82. The upper portion of the mixing chamber 74 may be contoured with some segments (10, 11, and 12) having different diameters for securing with, or fattening to, other parts in the analytical system 70.

Figure 10:
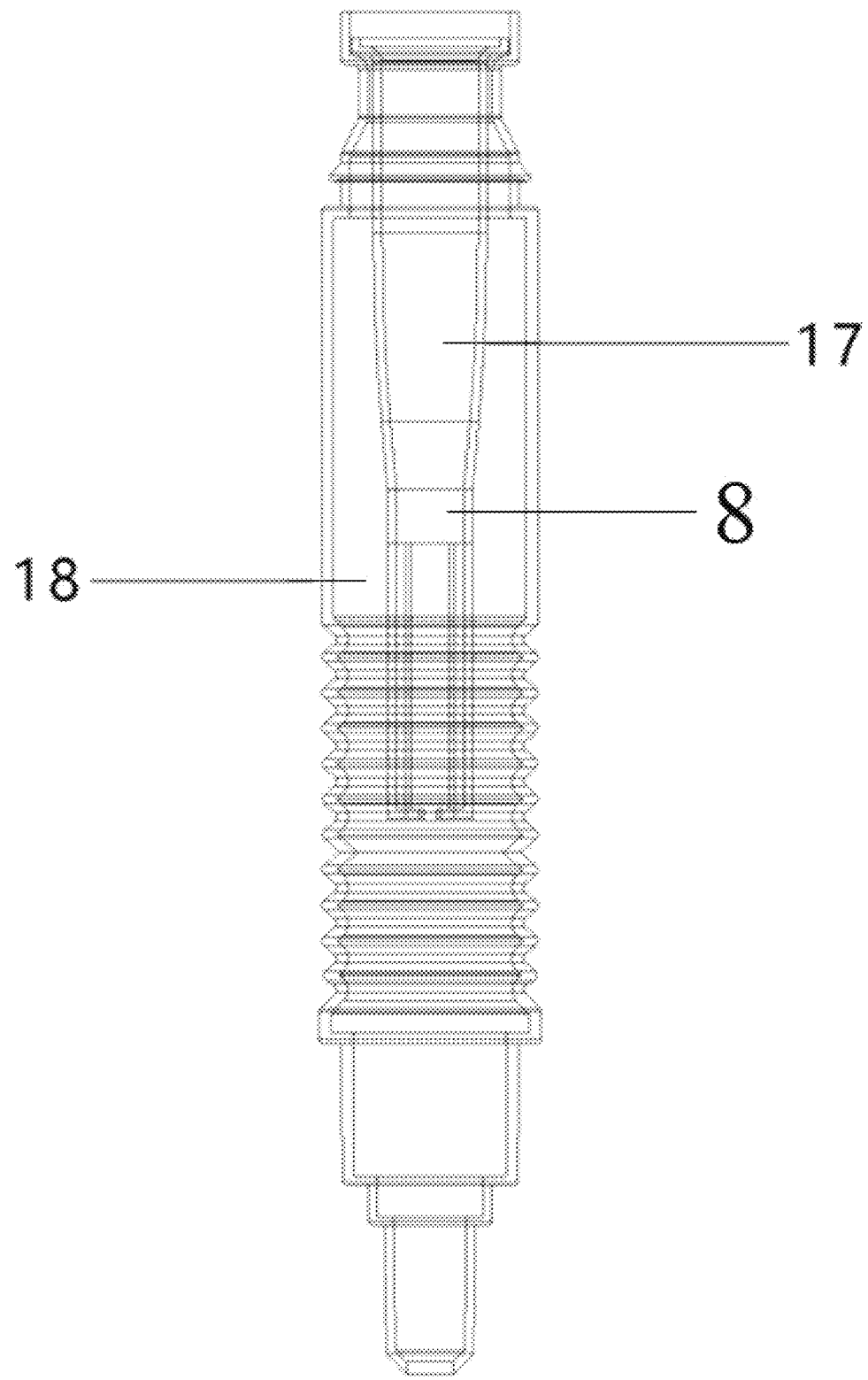
FIG. 10 schematically shows a sample funnel inserting into a mixing chamber in accordance with an exemplary embodiment of the present invention in accordance with an exemplary embodiment of the present invention.

For example, FIG. 10 shows that the funnel 85 is inserted into the mixing chamber 74 and secured to it. The internal space 18 of the mixing chamber 74 may be prefilled with a liquid such as a sample preservation fluid (not shown). The internal space 17 of the funnel 85 above the bottom opening 8 may be used to trap, retain and store the sample ("extra" or "surplus" sample, not shown) that was previously collected on the sample collection rod 5 but is wiped off from the rod 5 later by the bottom opening 8, except the sample within (i.e. filled into or aliquoted in) the spiral grooves 2 that cannot be wiped off from the rod 5 by the bottom opening 8. Therefore, the sample retained and stored in the internal space 17 is prevented from mixing with the liquid such as a sample preservation fluid prefilled in the mixing chamber 74 to formulate the sample preparation 84. Only the sample within (i.e. filled into or aliquoted in) the spiral grooves 2 that have not been (and could not be) wiped off from the rod 5 by the bottom opening 8 can enter the internal space 18. Preferably, facilitated by the fingers 9, substantially all (~100% of) the sample within (i.e. filled into or aliquoted in) the spiral grooves 2 is removed, shaken off, wiped off, scraped off, or unloaded/released from grooves 2, entering the internal space 18 and mixing with the liquid such as a sample preservation fluid prefilled in the mixing chamber 74 to formulate the sample preparation 84.

Figure 11:
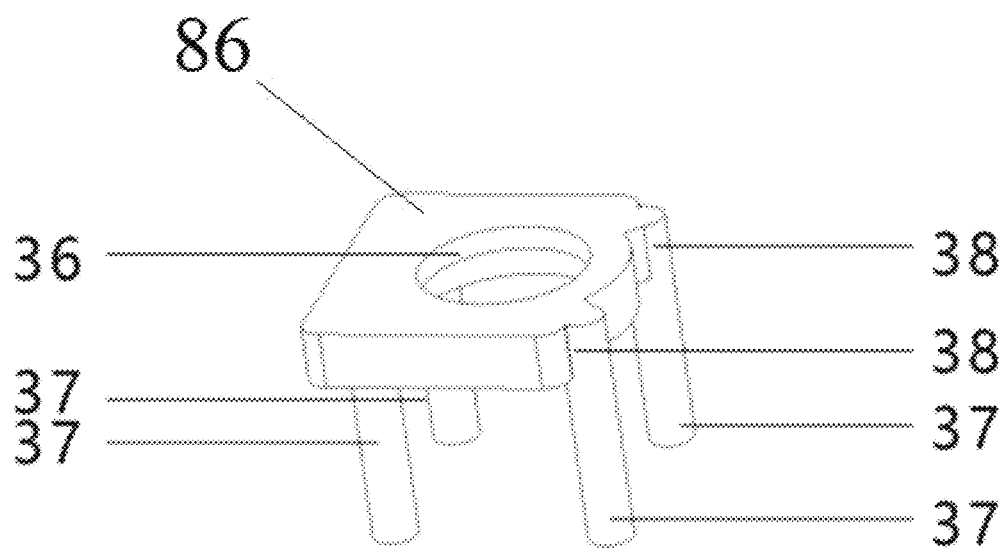
FIG. 11 depicts an upper member in the sample management module in accordance with an exemplary embodiment of the present invention.

In an exemplary embodiment as shown in FIG. 11, the upper member 82 may include a contacting portion 86 (e.g. "facing up") contactable against the contacting shoulder 15 (e.g. "facing down") of the mixing chamber 74. One, two, three, four or more downward legs 37 may be extended downwardly from the contacting portion 86. For example, the upper member 82 may be built like a table with 3 or 4 downward legs 37, and the tabletop functions as the contacting portion 86. The outlet opening 16 of the mixing chamber 74 may be inserted through a void, hole or opening 36 on the tabletop, and may move further downward to a position below the tabletop. The upper member 82 may include other contoured structure 38 for aligning with and securing to other parts in the analytical system 70.

Figure 12:
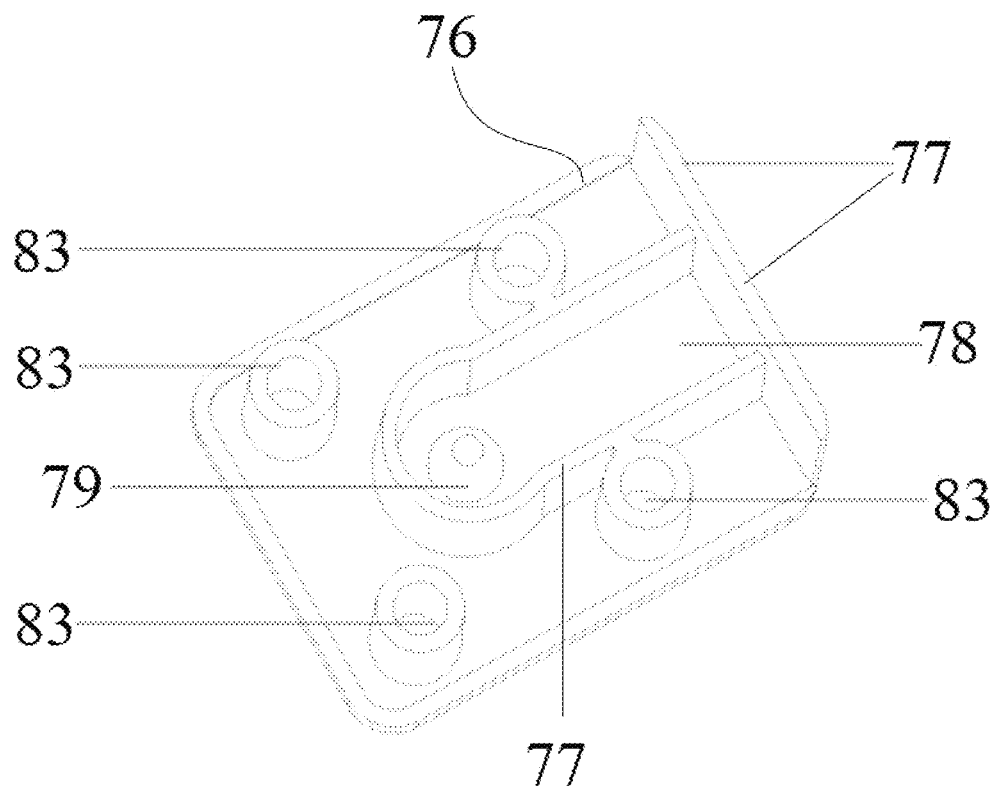
FIG. 12 is a perspective view of a sample tray and four alignment channels in the sample management module in accordance with an exemplary embodiment of the present invention.
Figure 13:
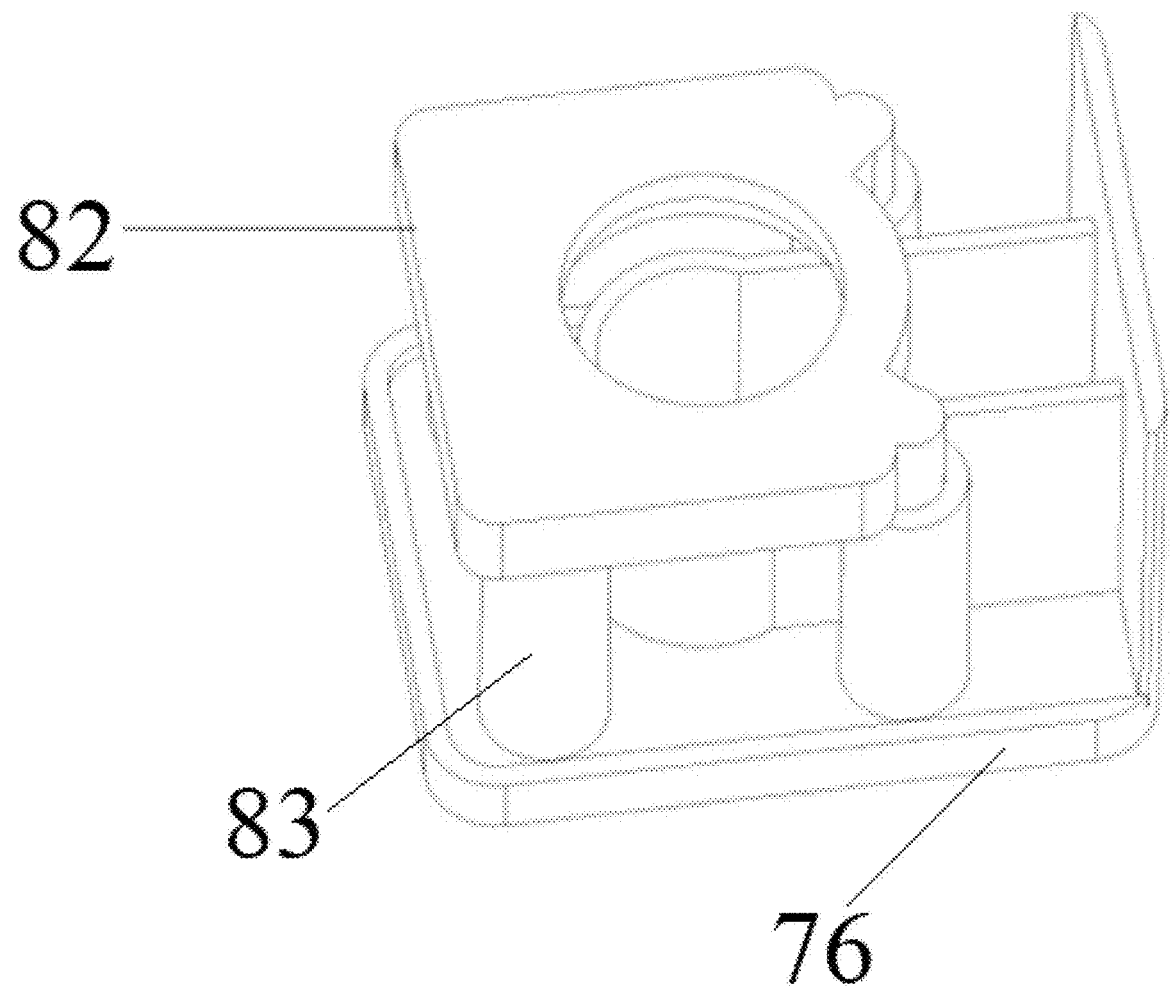
FIG. 13 shows the working relationship between a sample tray, four alignment channels and an upper member in accordance with an exemplary embodiment of the present invention.
Figure 15:
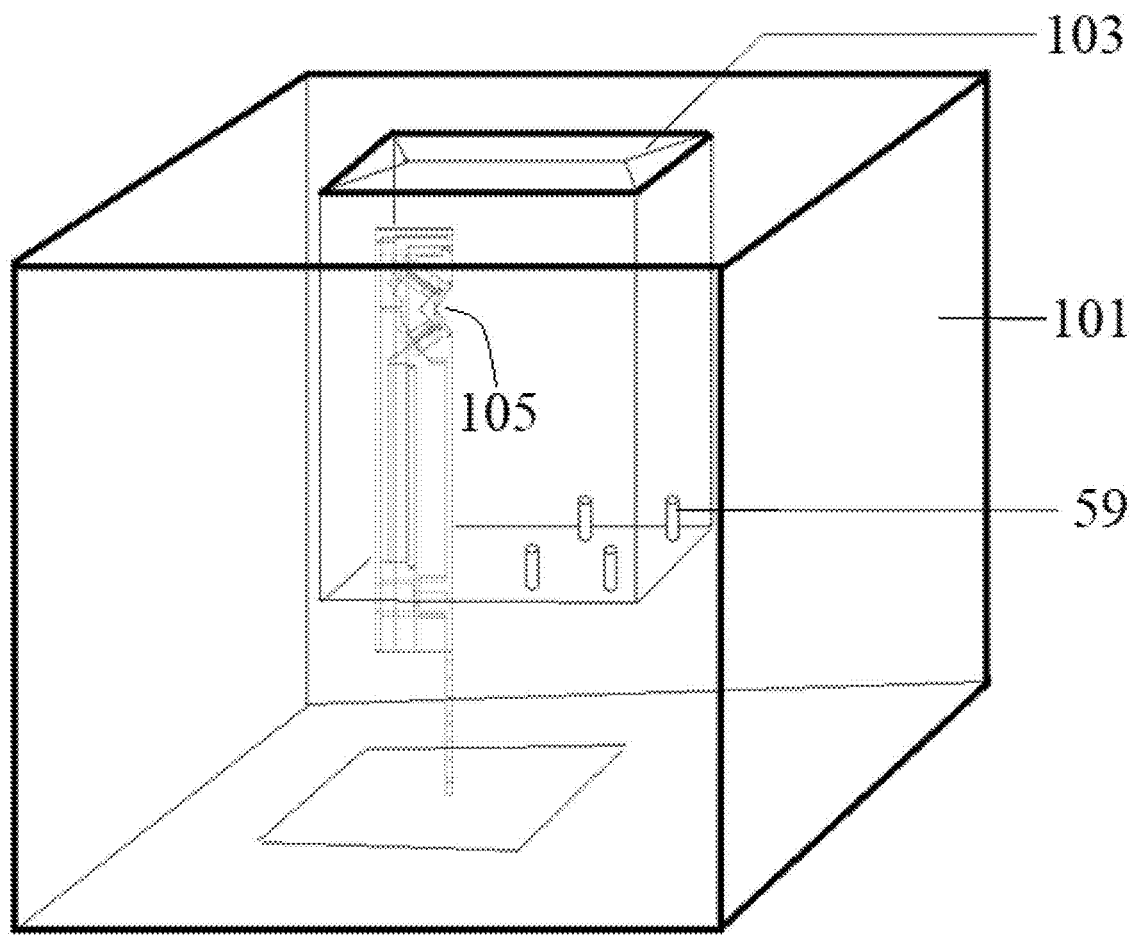
FIG. 15 depicts a first single unit of the analytical system for home users in accordance with an exemplary embodiment of the present invention.

The lower member 81 may include a same number of upward leg(s) 59 (as shown in FIG. 15, and will be described later) as the downward leg(s) 37. The upward leg(s) 59 is (are) contactable to the downward leg(s) 37. In preferred embodiments, the pressure delivery assembly 80 further comprises a same number of alignment channel(s) 83 as the upward leg(s) 59 or downward leg(s) 37, to align the movement of the upward leg(s) 59 and the movement of the downward leg(s) 37, before the upward leg(s) 59 and the downward leg(s) 37 meet and contact each other within the alignment channel(s) 83. In a particularly preferred embodiment as shown in FIG. 12, the sample tray 76 and the alignment channel(s) 83 are integrated to each other, and manufactured as a single piece. A receptacle area 78 of the sample tray 76 is formed by a raised and enclosed rim 77, and is configured for receiving an amount of the sample preparation 84 released from the mixing chamber 74. An island 79 is protruded out from the receptacle area 78. Before releasing the sample preparation 84, the island 79 engages with (or plugs into) the outlet opening 75 of the mixing chamber 74 and seals the outlet opening 75 to prevent releasing of the sample preparation 84 through it. Although FIG. 12 shows that the alignment channel(s) 83 go through an area of the sample tray 76 other than the receptacle area 78, it should be appreciated that the alignment channel(s) 83 may go through the receptacle area 78 and/or an area of the sample tray 76 other than the receptacle area 78. FIG. 13 shows an exemplary working relationship between the sample tray 76, the alignment channels 83 and the upper member 82.

Figure 14:
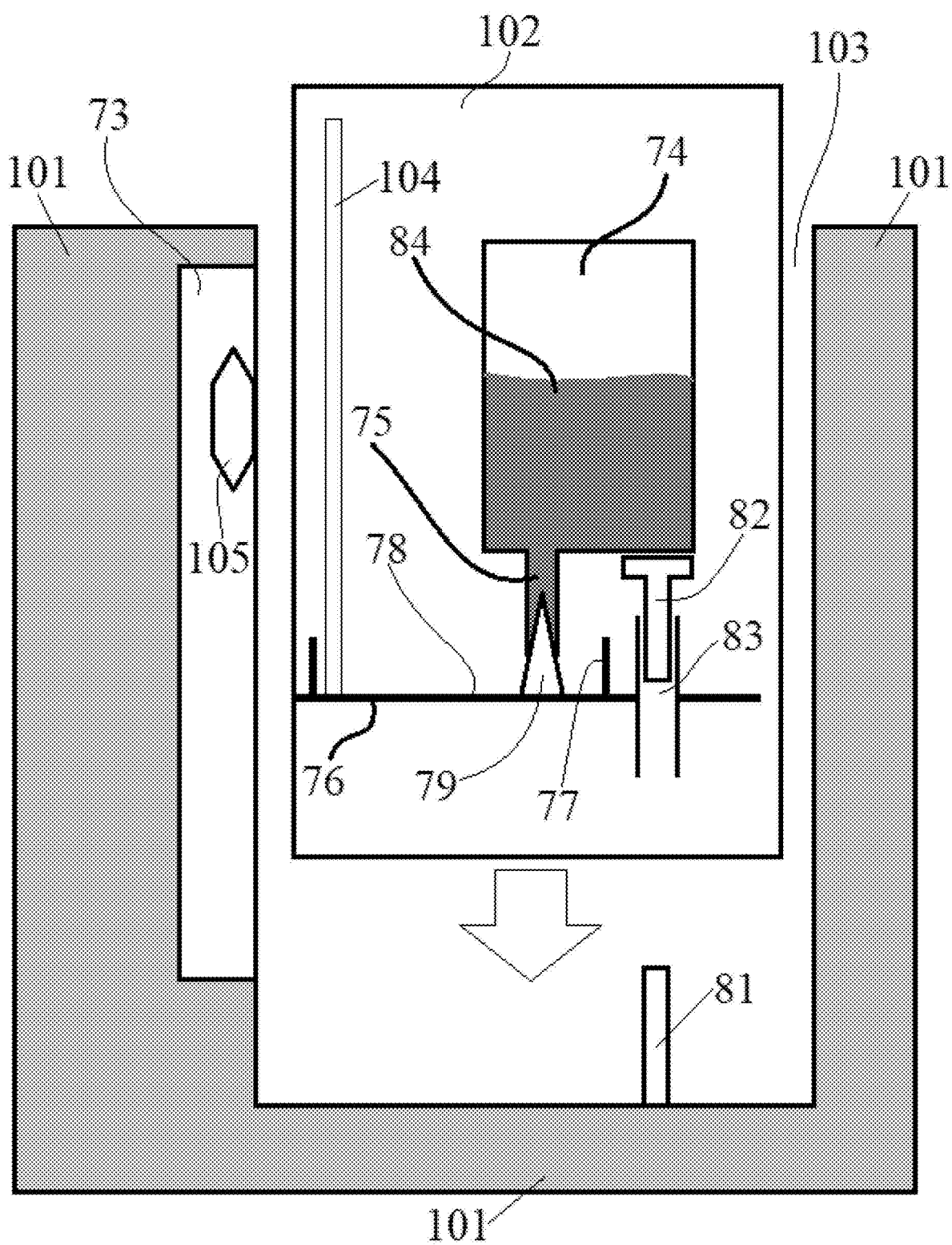
FIG. 14 schematically shows an analytical system for home users in accordance with an exemplary embodiment of the present invention.

In various embodiments of the invention as illustrated in FIG. 14, the sample analysis module 73 and the lower member 81 are built into a first single unit 101 (colloquially "detector," "detector box," or similar term for a home user). The mixing chamber 74, the sample tray 76 and the upper member 82 are built into a second single unit 102 (colloquially "sample box" or similar term for a home user). The first single unit 101 may include a harbor/slot 103 for receiving and securing the second single unit 102. In one embodiment, the invention is implemented with an integrated sample box (as an embodiment of the second single unit 102) and a supporting potable detector (as an embodiment of the first single unit 101) to perform quantitative FIT in one step operating/performance, and to detect both hemoglobin and transferrin. The integrated sample box with designed structure and necessary parts is sufficient to perform quantitative fecal immunochemical test in a one-step operation. The system can fulfill full task of fecal sample collection and quantitative fecal immunochemical test with only one step performance. The system is particularly useful for point-of-care or home based testing.

In some embodiments, the second single unit 102 includes one or more alignment channels 83 to align the lower member 81's movement and the upper member 82's movement before the two members (81, 82) meet and contact each other, when the second single unit 102 is inserted into the harbor/slot 103. Preferably, the one or more alignment channels 83 are integrated with the sample tray 76.

In preferred embodiments, the second single unit 102 includes a chromatography medium or a test strip 104 with e.g. antibody, such as a chromatography paper 104 extending from the receptacle area 78 and configured to absorb the sample preparation 84 therein. The first single unit 101 includes a detector 105 for detecting a signal (e.g. a stimulated signal) emitted from the test strip 104 after it absorbs the sample preparation 84.

FIG. 15 illustrates an embodiment of the first single unit 101 with 3-4 upward legs 59 as a part of the lower member 81, an example of the supporting potable detector as mentioned above. The upward legs 59 are contactable to the downward legs 37 as shown in FIG. 11. In preferred embodiments, the pressure delivery assembly 80 further comprises a same number of (e.g. 3-4) alignment channels 83 as the upward legs 59 or downward legs 37, to align the movement of the upward legs 59 and the movement of the downward legs 37, before the upward legs 59 and the downward legs 37 meet and contact each other within the alignment channels 83.

Figure 16:
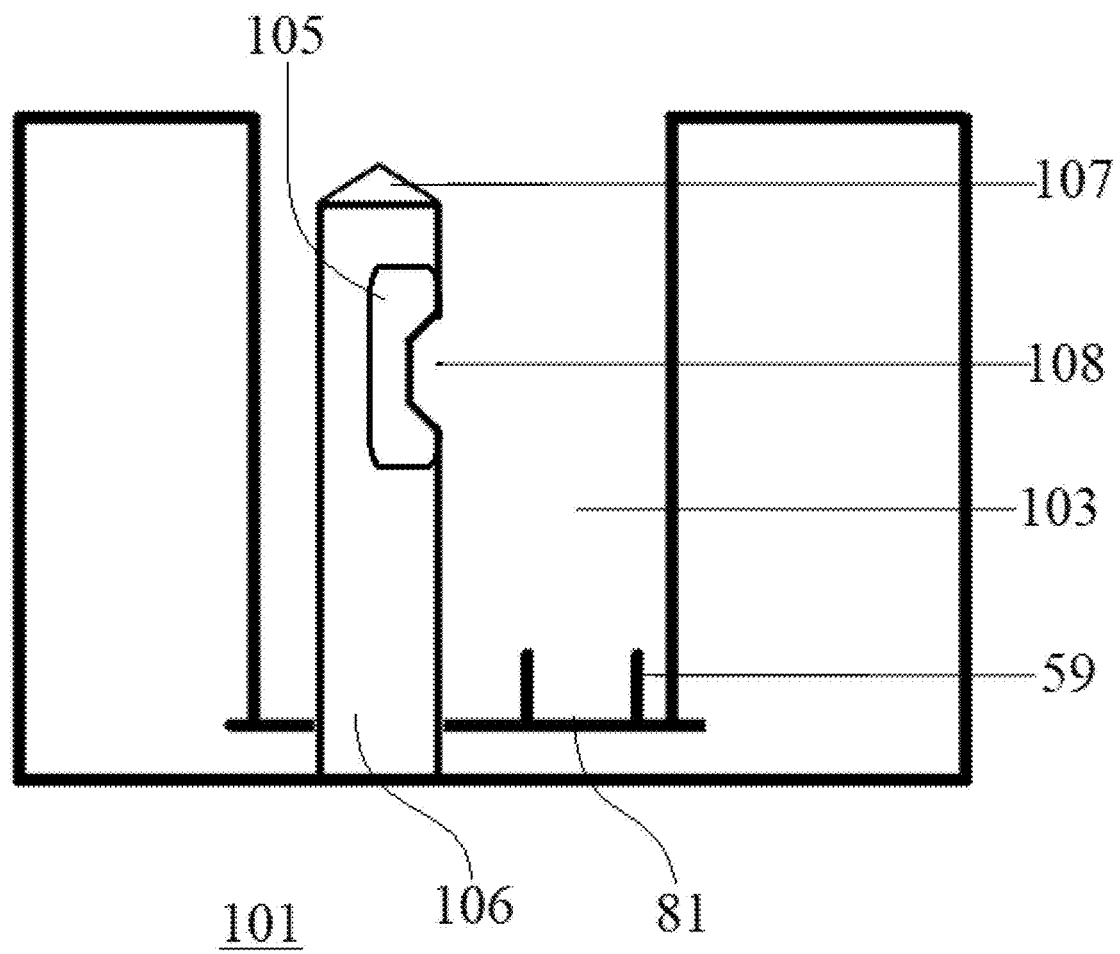
FIG. 16 schematically illustrates a first single unit of the analytical system for home users in accordance with an exemplary embodiment of the present invention.

FIG. 16 is a cross-sectional view of an embodiment of the first single unit 101 with upward legs 59 as a part of the lower member 81, an example of the supporting potable detector as mentioned above. The first single unit 101 includes a harbor/slot 103 for receiving and securing the second single unit 102 (not shown in FIG. 16). A tower 106 is placed within the harbor/slot 103, and the tower 106 may optionally have a sharp top 107. Within the tower 106 is a detector 105 for detecting a signal (e.g. a stimulated signal) emitted from the chromatography medium 104 and through a detector window 108, after the medium 104 absorbs the sample preparation 84.

As an example of the sample box mentioned above, FIG. 17 illustrates an embodiment of the second unit 102 configured for fitting into, and working with, the first single unit 101 as shown in FIG. 16. A tower receptacle 112 is configured to receive and harbor the tower 106. A receptacle window 111 in a spacer 114 is designed to face to, and overlap with, detector window 108, after the tower 106 is inserted into the tower receptacle 112. The detector 105 can then detect a signal (e.g. a stimulated signal) emitted from the chromatography medium 104 through both the detector window 108 and the receptacle window 111. The entrance of the tower receptacle 112 may be sealed with a thin film 110. When the second single unit 102 is inserted downward into the harbor/slot 103, the tower 106 is simultaneously inserted upward (relatively speaking) into the tower receptacle 112, and the thin film 110 will be "tear open," pierced open, or penetrated through by the sharp top 107 of the tower 106. A certain amount of liquid 113 such as a sample preservation fluid (e.g. a "fecal sample preservation buffer") is preloaded in the mixing chamber 74, and the second unit 102 may further include a cover 109 to prevent the liquid 113 from evaporating away from the mixing chamber 74 through funnel 85.

Figure 18:
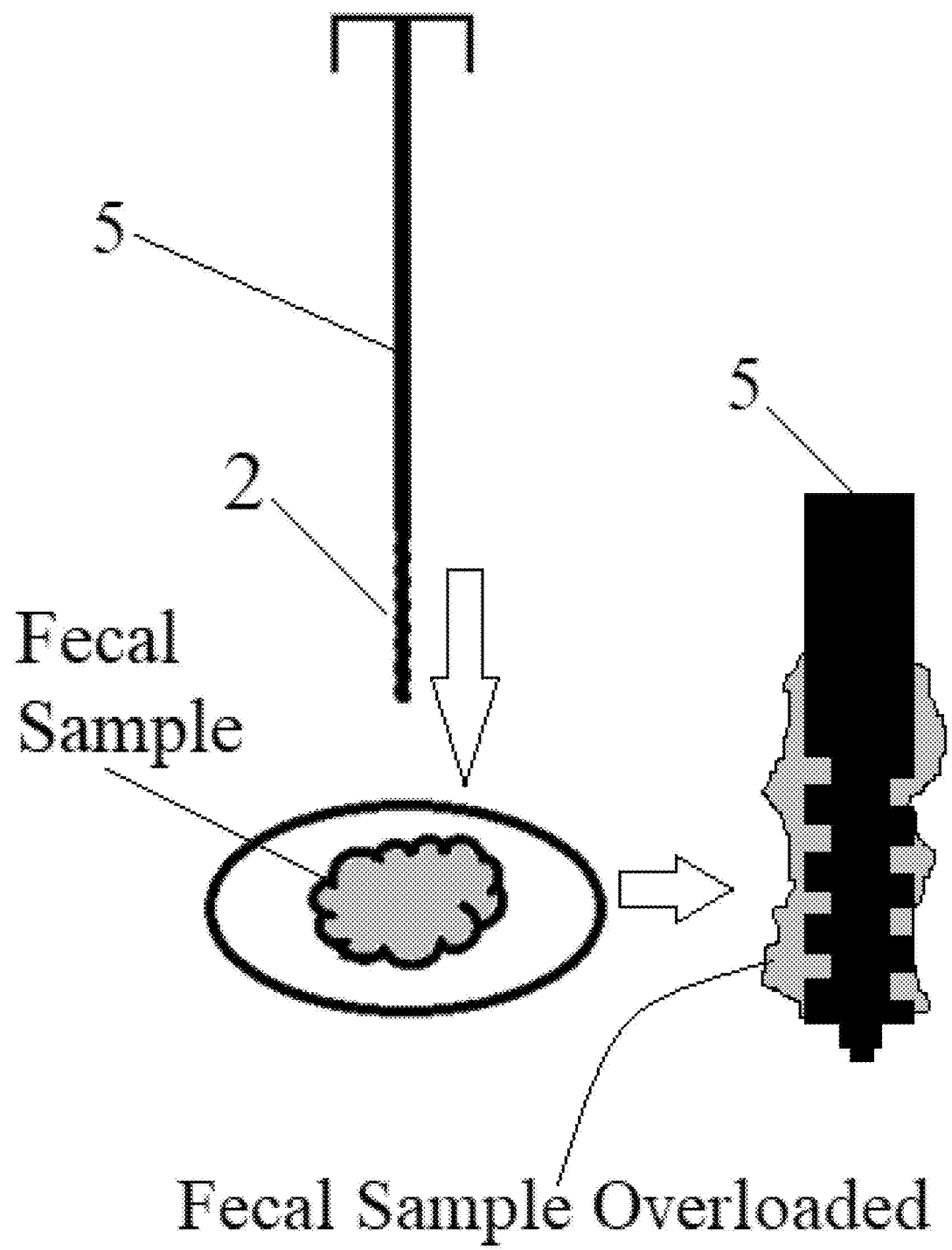
FIG. 18 illustrates a sample collection rod taking a fecal sample in accordance with an exemplary embodiment of the present invention.

As described above and illustrated in FIG. 4, the method of the invention includes step (1) of collecting a sample with the sample collection module 71. FIG. 18 illustrates the sample collection rod 5 is used to take a fecal sample. The sampling operation should preferably ensure that the entire spiral grooves 2 are completely inserted into the fecal sample, and fully filled with, or overloaded with, the fecal sample. Overloading of the fecal sample on the sample collection rod 5 is acceptable, because the bottom opening 8 of the funnel 85 will remove any extra samples on rod 5. For example, spiral grooves 2 can carry about 50 mg of fecal sample.

Figure 19:
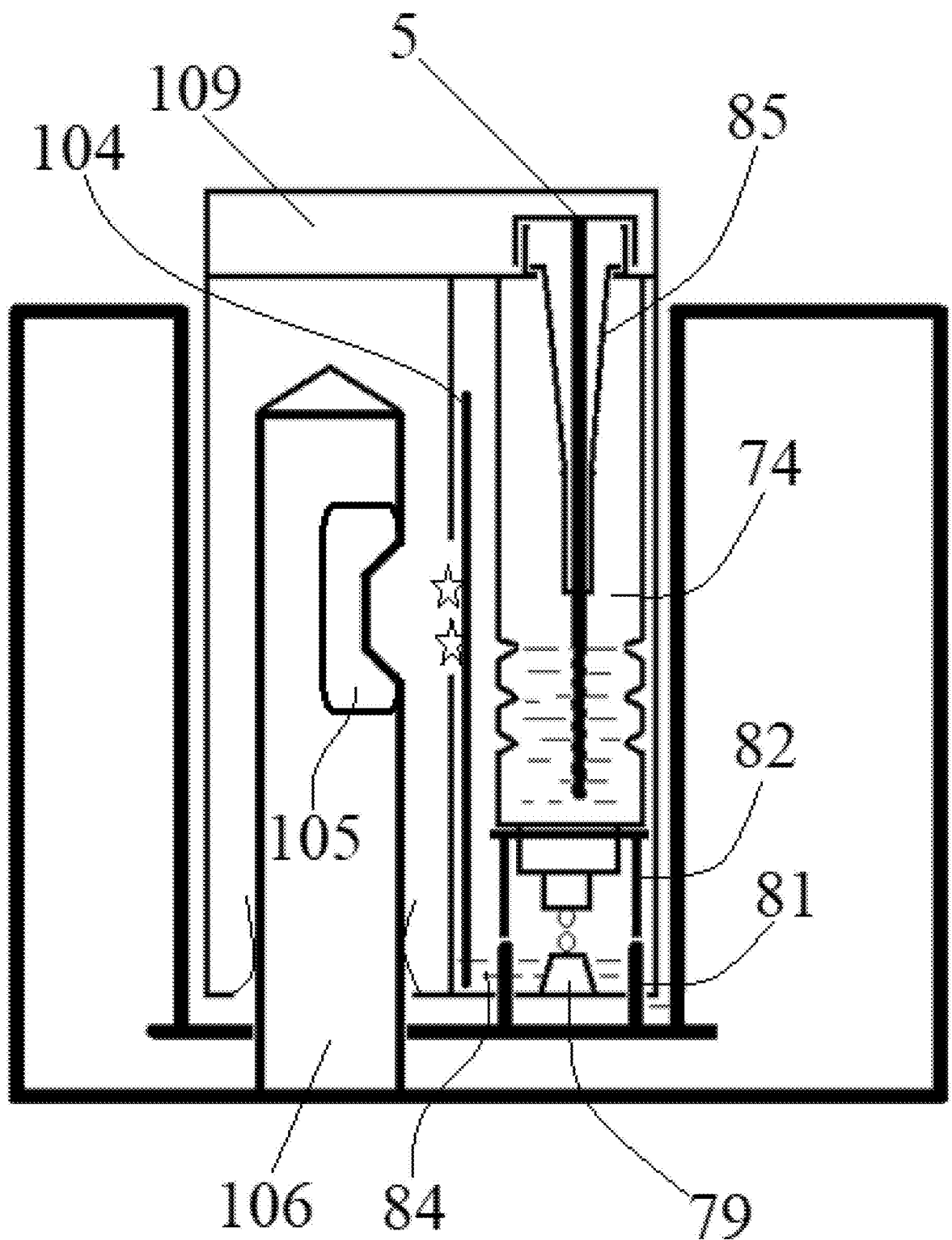
FIG. 19 schematically illustrates the first and second single units of the analytical system are working with each other in accordance with an exemplary embodiment of the present invention.

In FIG. 19, the cap or cover 109 is first removed. The sample collection rod 5 overloaded with the fecal sample is then pushed all the way down into the mixing chamber 74 of the second unit 102 through the funnel 85. The sample preparation 84 is formed in the mixing chamber 74. The cover 109 is preferably secured back to the second unit 102. Then, the second single unit 102 is inserted downward into the harbor/slot 103, and the tower 106 is simultaneously inserted upward (relatively speaking) into the tower receptacle 112. During this single "insertion" step, an amount (e.g. about 120 microliters) of the sample preparation 84 is released from the mixing chamber 74 into the receptacle area 78. The lower end of the chromatography medium 104 in the second unit 102 with e.g. antibody, then starts to absorb the sample preparation 84 in the receptacle area 78. This will initiate the sample analysis procedure with detector 105.

Figure 20:
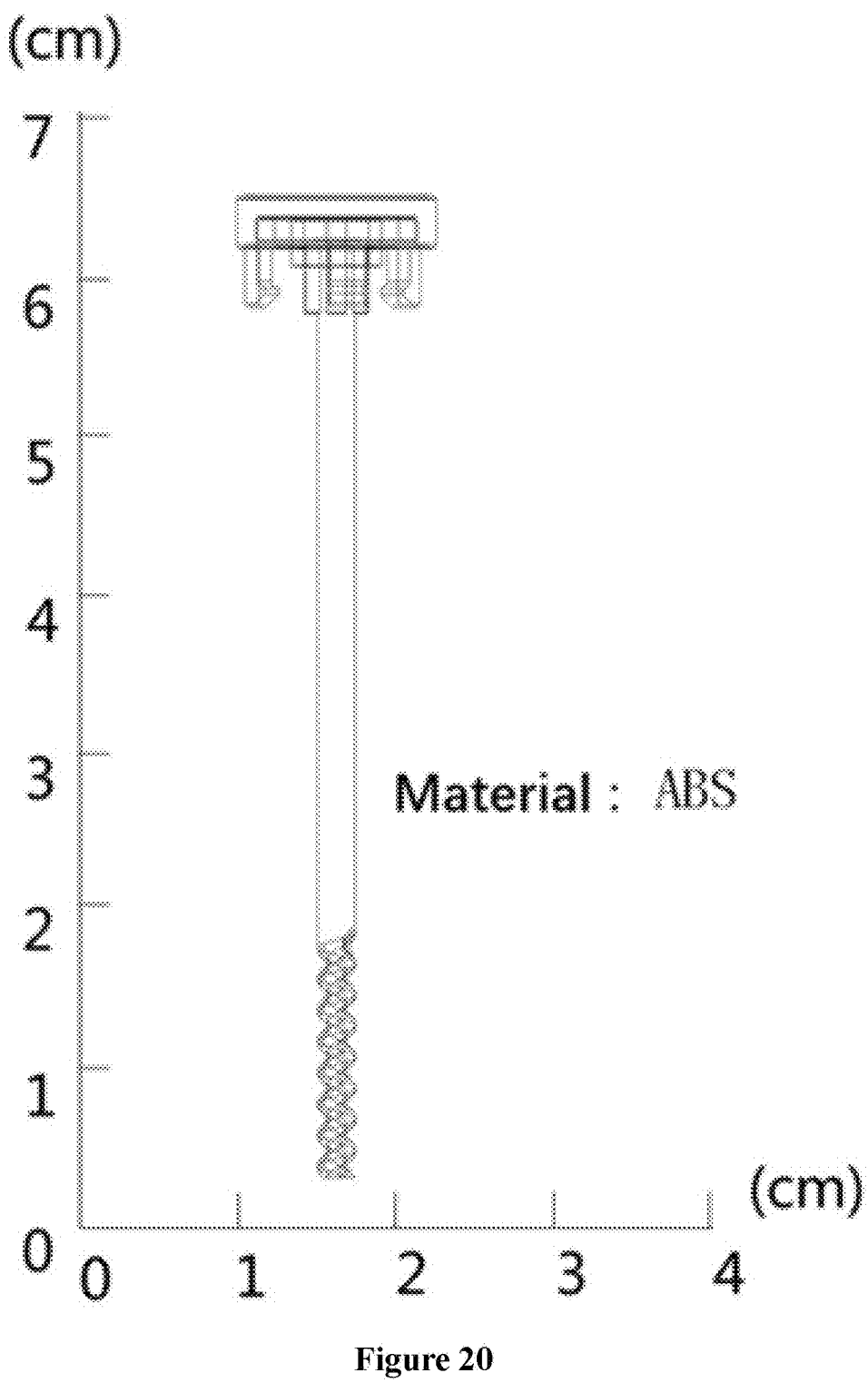
FIG. 20 indicates the specific size and construction material of a sample collection rod in accordance with an exemplary embodiment of the present invention.

FIG. 20 shows a specific size and construction material of the sample collection rod 5 as shown in FIG. 5. In preferred embodiments of the invention, the sample collection rod 5 may be made of acrylonitrile butadiene styrene (ABS). The longitudinal length of the rod 5 may be from 5 cm to 7 cm such as 6 cm, and the diameter of the locking cap 1 may be from 0.5 cm to 2.5 cm.

Figure 21:
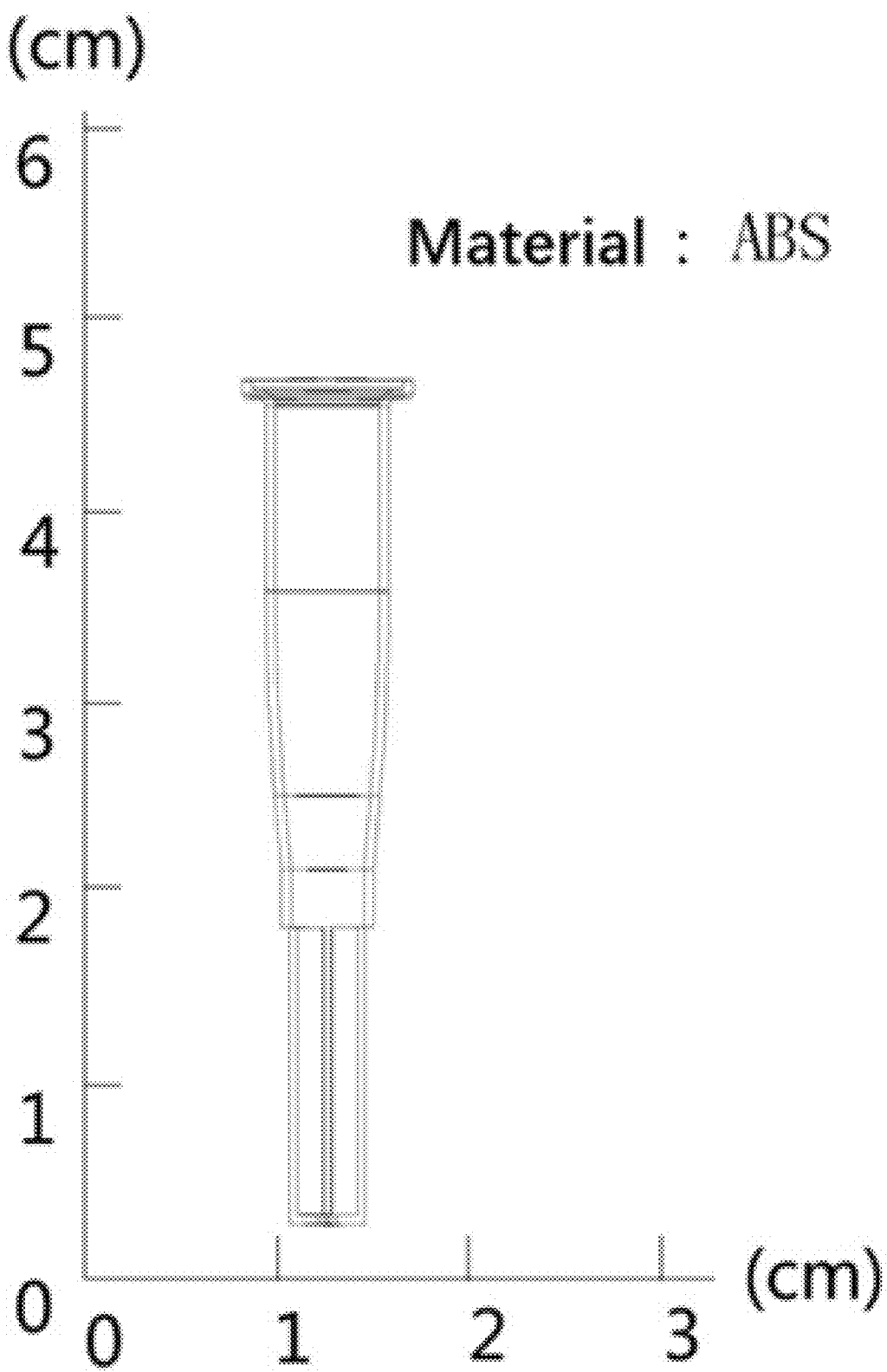
FIG. 21 indicates the specific size and construction material of a sample limiting funnel in accordance with an exemplary embodiment of the present invention.

FIG. 21 shows a specific size and construction material of the funnel 85 ("fecal samples limiting funnel") as shown in FIG. 7. In preferred embodiments of the invention, the funnel 85 may be made of acrylonitrile butadiene styrene (ABS). The longitudinal length of the funnel 85 may be from 3 cm to 5 cm, and the diameter of the funnel 85 may be decreased from about 0.8 cm down to about 0.2 cm.

Figure 22:
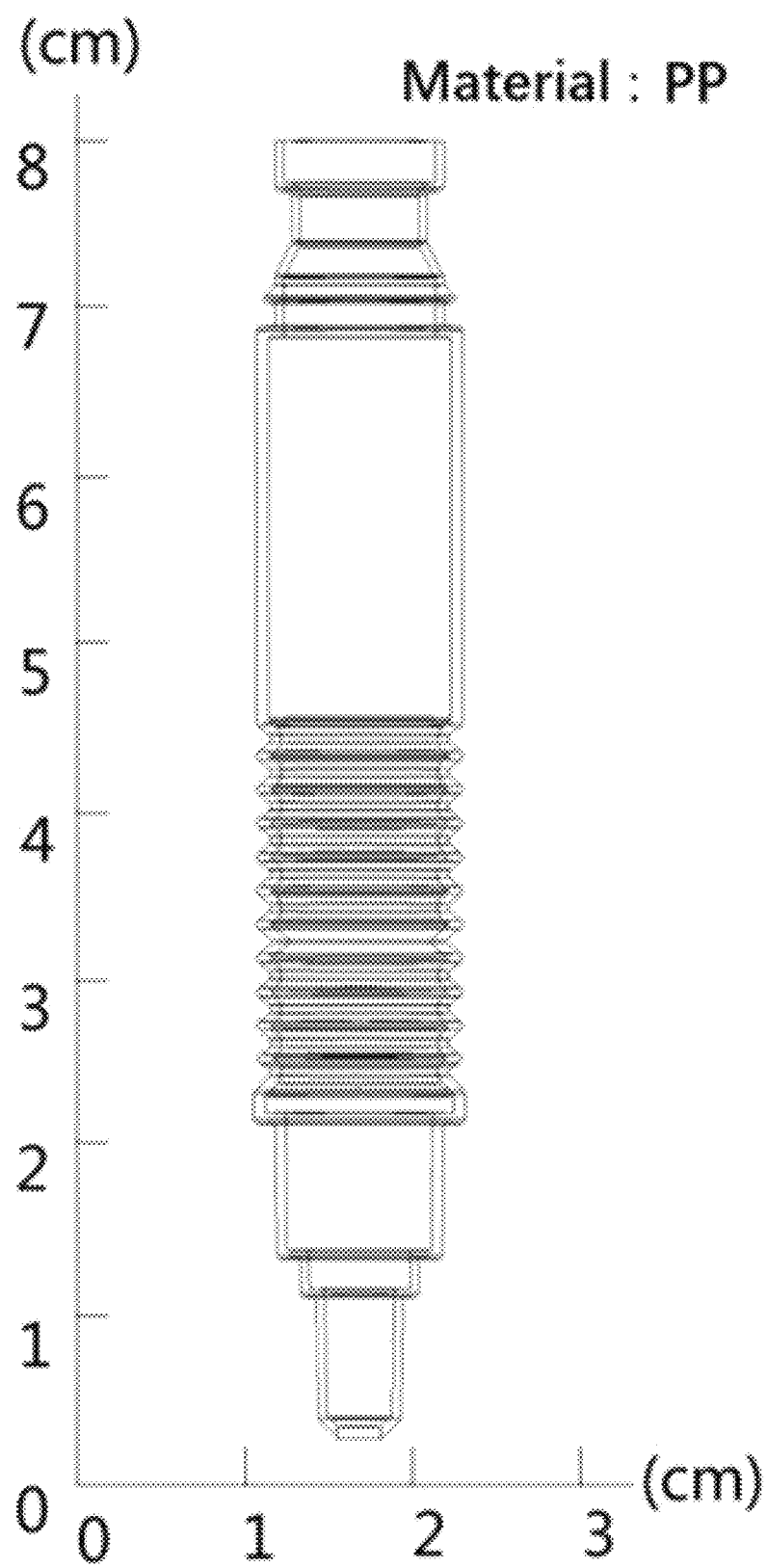
FIG. 22 indicates the specific size and construction material of a mixing chamber in accordance with an exemplary embodiment of the present invention.

FIG. 22 shows a specific size and construction material of the mixing chamber 74 (a "telescopic foldable sample storage tube") as shown in FIG. 9. In preferred embodiments of the invention, the mixing chamber 74 may be made of polypropylene (PP). The longitudinal length of the mixing chamber 74 may be from 7 cm to 9 cm, and the diameter of the mixing chamber 74 may vary between 0.2 cm and 2.0 cm.

Figure 17:
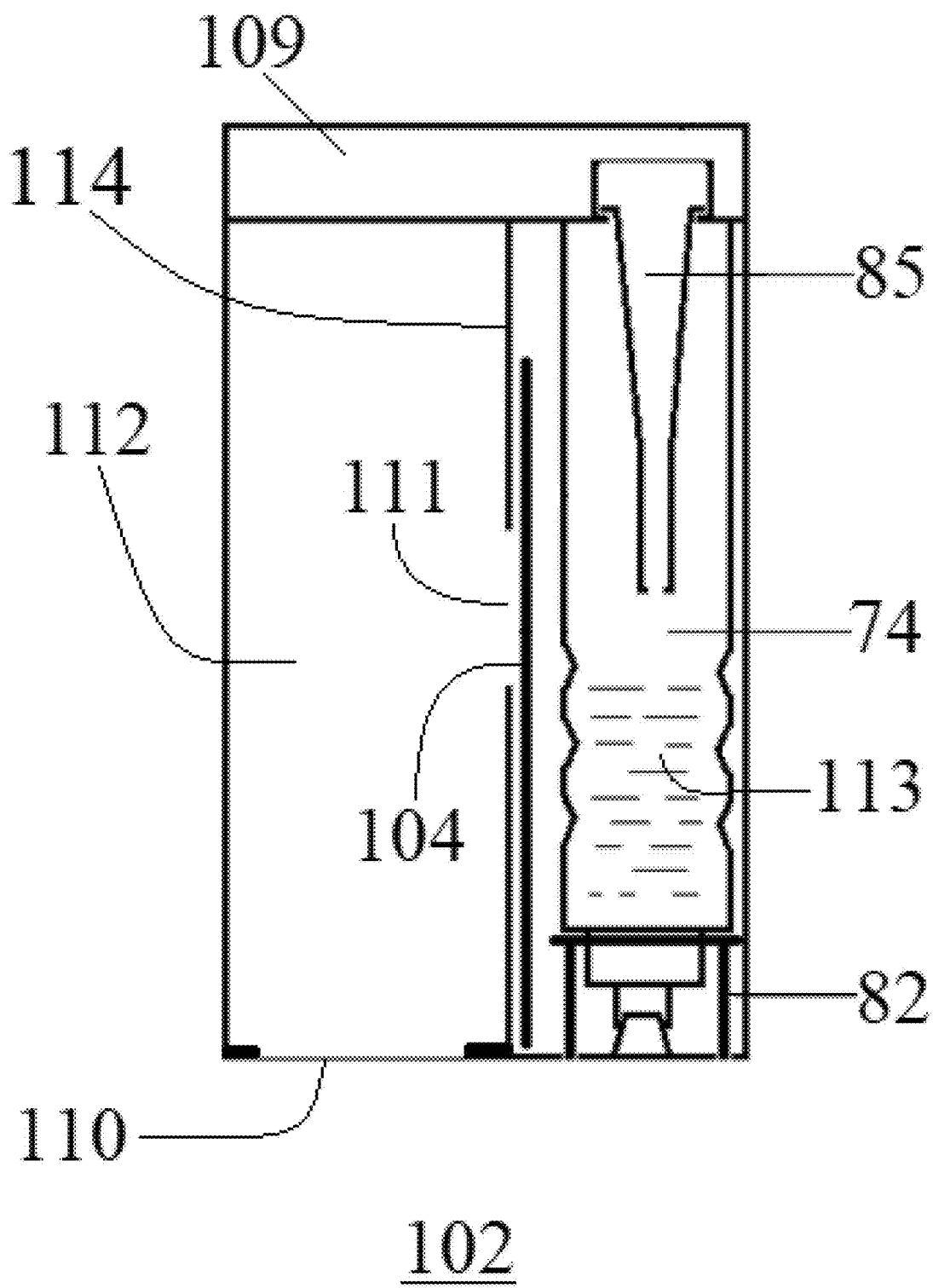
FIG. 17 schematically illustrates a second single unit of the analytical system for home users in accordance with an exemplary embodiment of the present invention.
Figure 23:
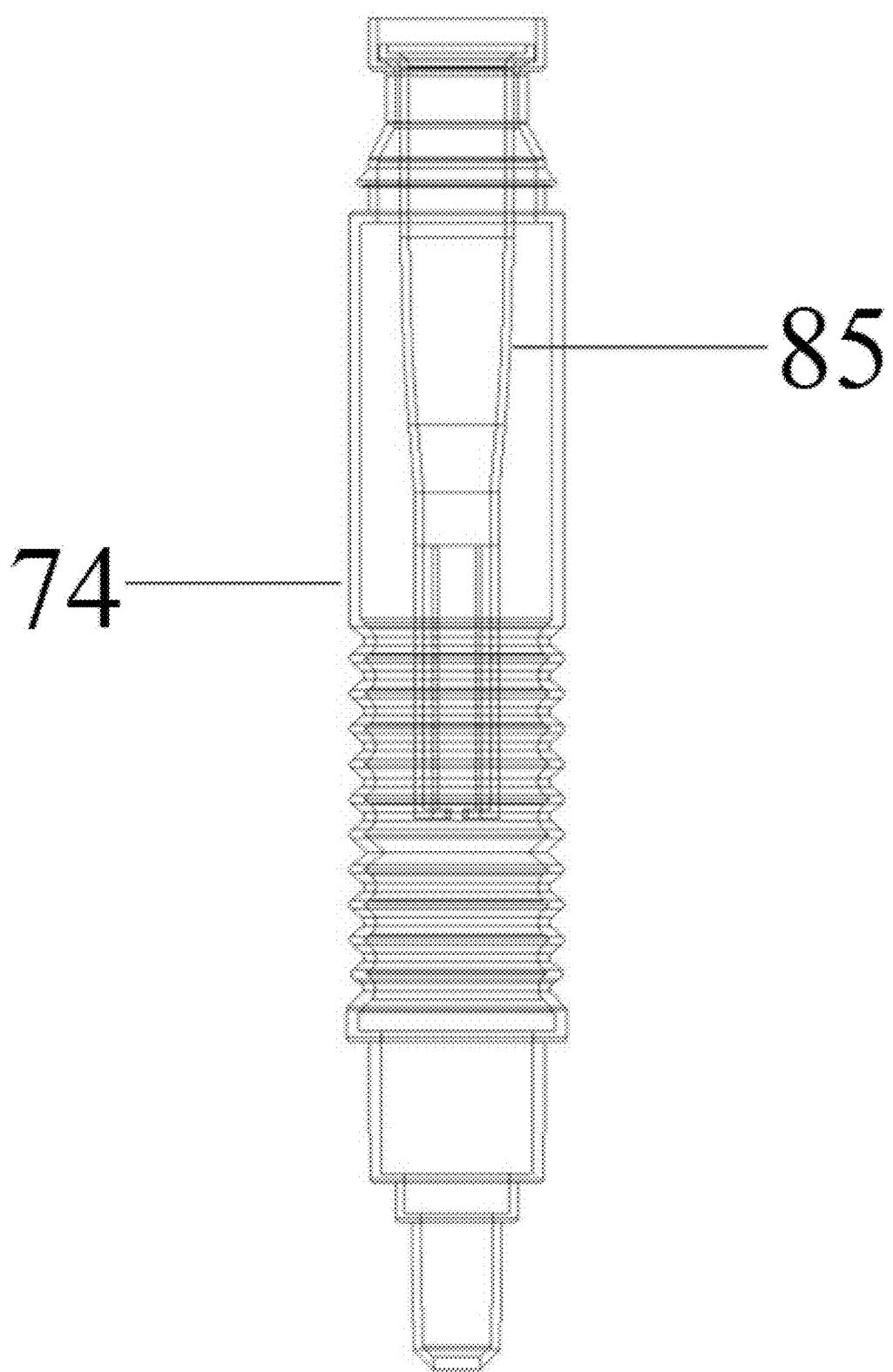
FIG. 23 shows a sample limiting funnel inserted into and secured to a mixing chamber in accordance with an exemplary embodiment of the present invention.
Figure 24:
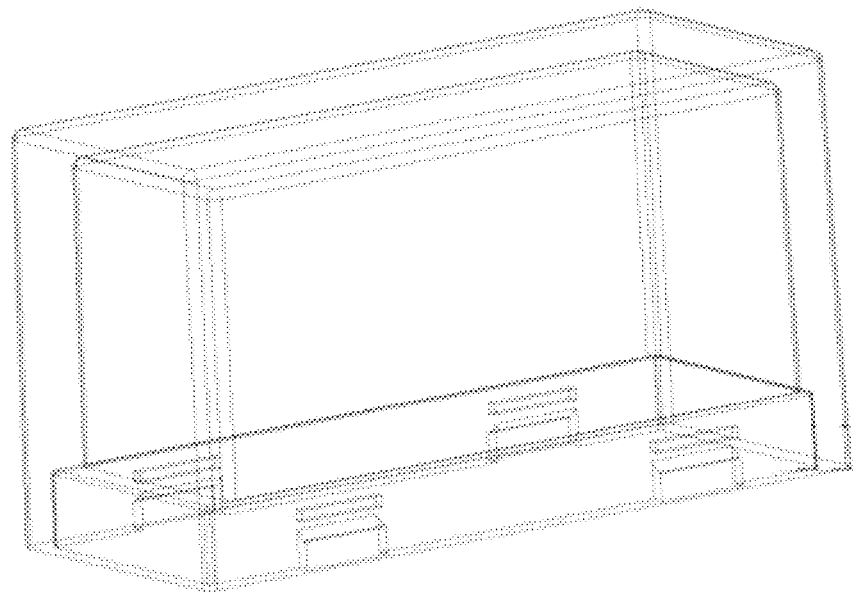
FIG. 24 demonstrates a cap/cover of the second single unit of the analytical system for home users in accordance with an exemplary embodiment of the present invention.
Figure 25:
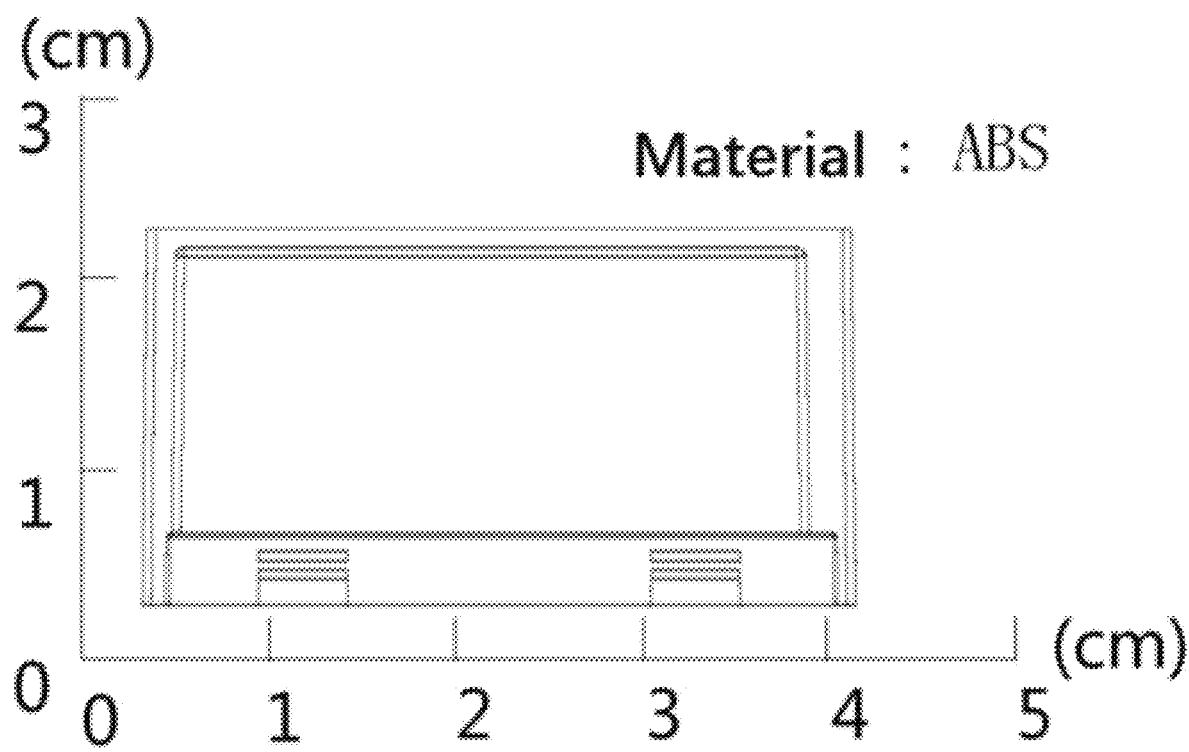
FIG. 25 indicates the specific size and construction material of a cap/cover of the second single unit of the analytical system for home users in accordance with an exemplary embodiment of the present invention.

FIG. 23 shows that the funnel 85 of FIG. 21 is inserted into the mixing chamber 74 of FIG. 22 and secured to it. FIG. 24 shows a specific design of the cap/cover 109 (colloquially "sample box upper cap") as shown in FIG. 17. Particularly, FIG. 25 shows a specific size and construction material of the cover 109 as shown in FIG. 24. In preferred embodiments of the invention, the cover 109 may be made of acrylonitrile butadiene styrene (ABS). The height of the cover 109 may be from 1 cm to 3 cm, and the width of the cover 109 may be from 3 cm to 5 cm. An upper tearable sealing film is used to seal sample box from the top. A bottom sealing film is used to seal sample box from bottom. These films maintain the sample box completely sealed.

Figure 26:
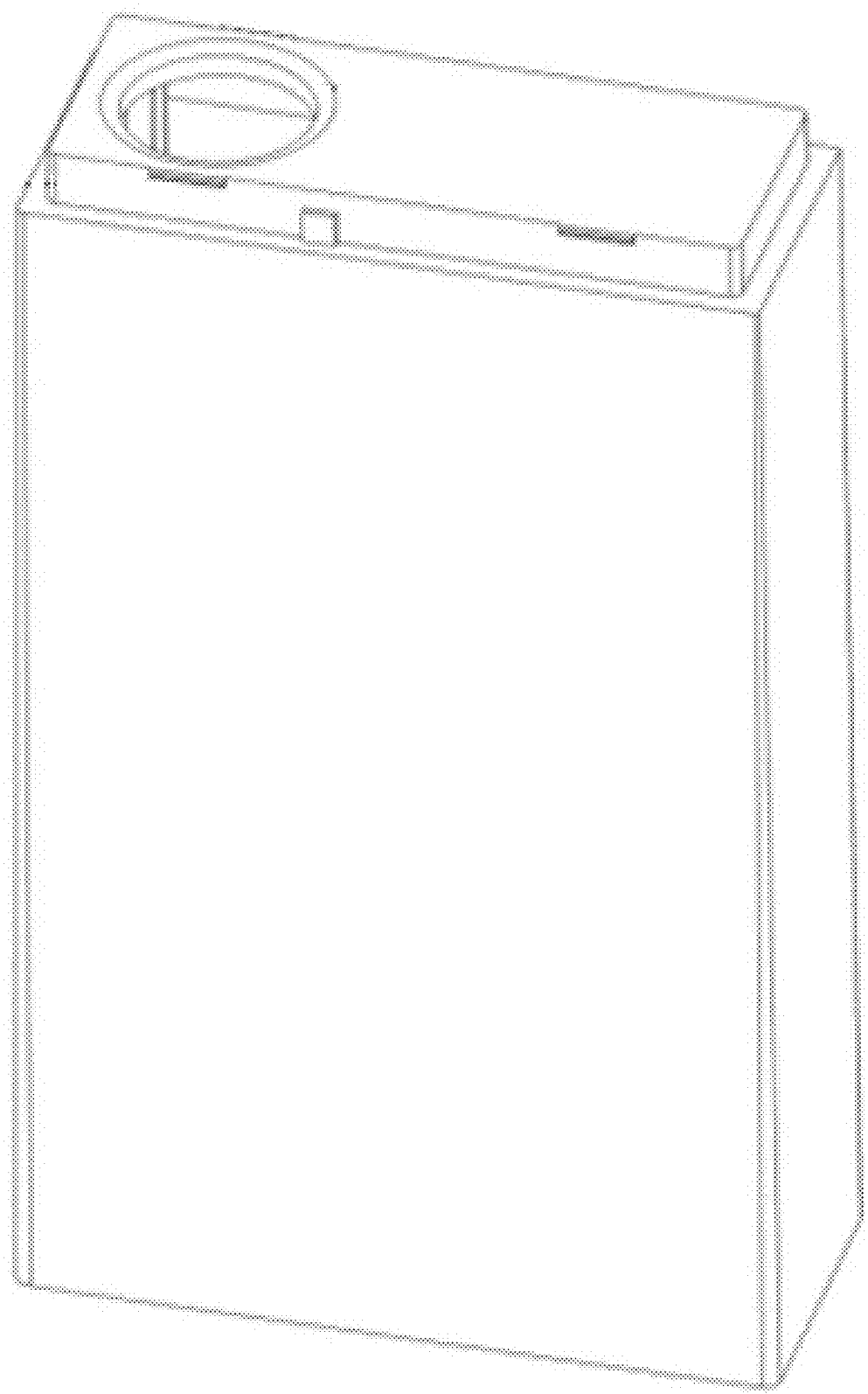
FIG. 26 is a specific "sample box" design of the second unit as shown in FIG. 17 in accordance with an exemplary embodiment of the present invention.

FIG. 26 shows a specific "sample box" design of the second unit 102 as shown in FIG. 17, before it is assembled with the cover 109 of FIG. 24, the funnel 85 of FIG. 21, and the mixing chamber 74 of FIG. 22.

Figure 27:
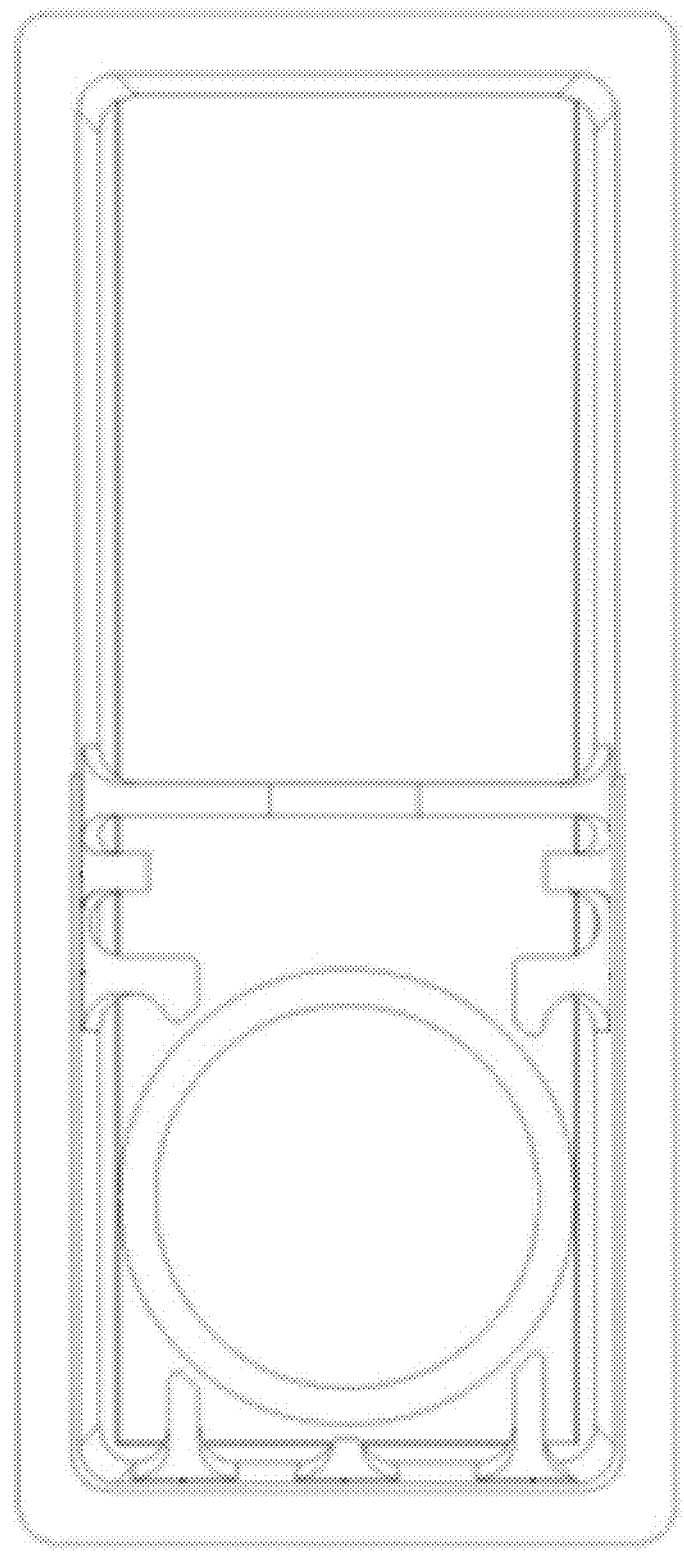
FIG. 27 is a cross-sectional bottom view of the "sample box" as shown in FIG. 26 in accordance with an exemplary embodiment of the present invention.
Figure 28:
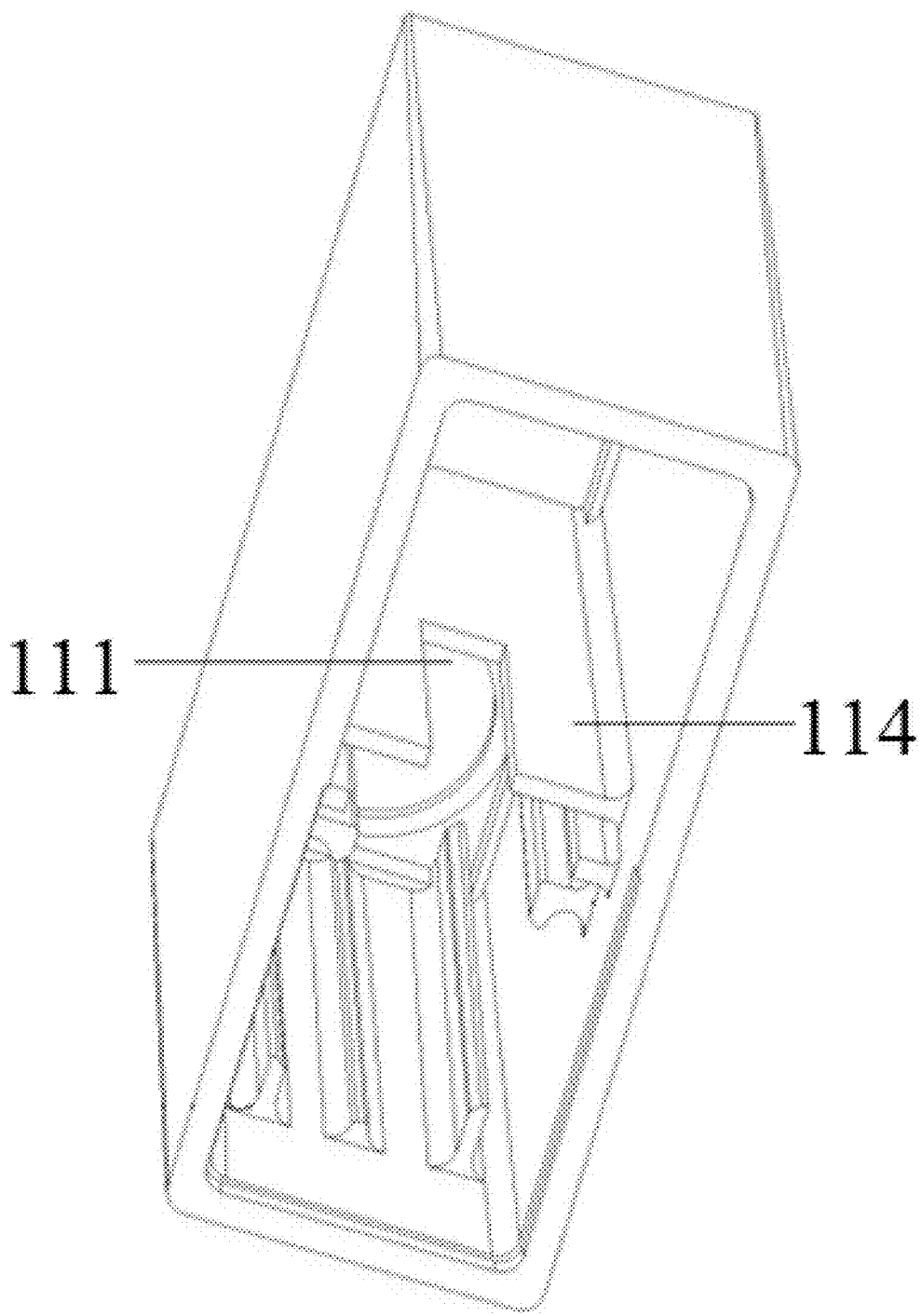
FIG. 28 is a cut-open top perspective view of the "sample box" as shown in FIG. 26 in accordance with an exemplary embodiment of the present invention.

While FIG. 27 is a cross-sectional bottom view of the second unit 102 as shown in FIG. 26, FIG. 28 is a cut-open top perspective view thereof. Desiccant can be placed in any proper location inside the sample box.

Figure 29:
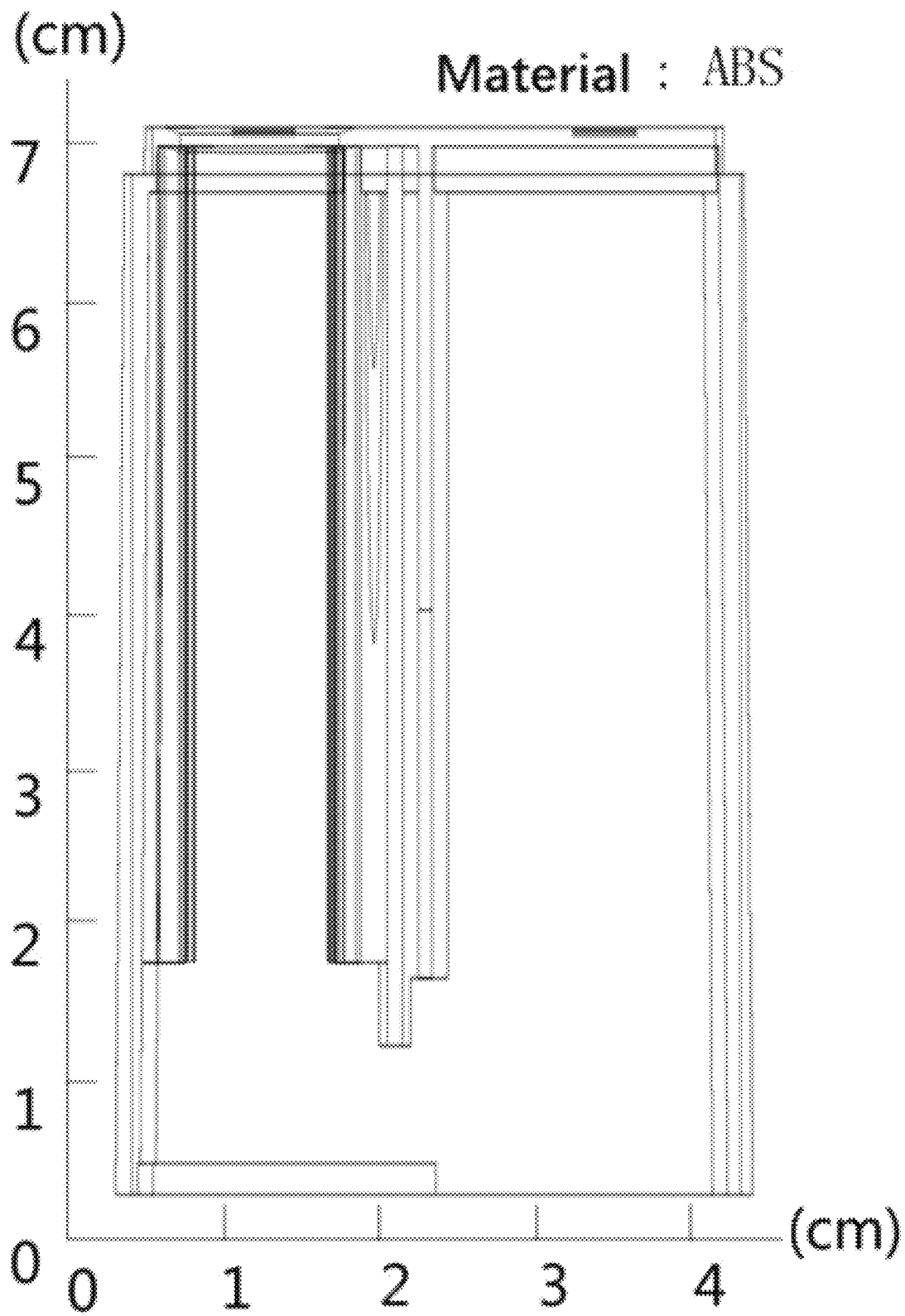
FIG. 29 indicates the specific size and construction material of a part of the "sample box" as shown in FIG. 26 in accordance with an exemplary embodiment of the present invention.

FIG. 29 shows a specific size and construction material of the second unit 102 as shown in FIG. 26 (not including the portion as shown in FIG. 13). In preferred embodiments of the invention, this part may be made of acrylonitrile butadiene styrene (ABS). The height of may be from 6 cm to 8 cm, and the width may be from 3 cm to 5 cm.

Figure 30:
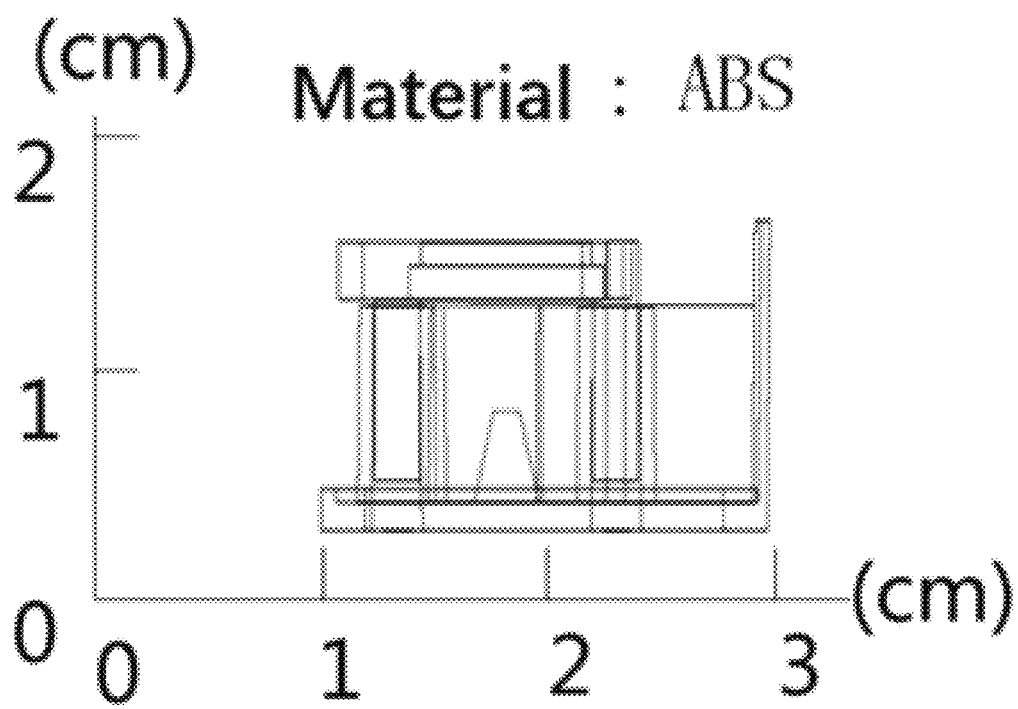
FIG. 30 indicates the specific size and construction material of another part of the "sample box" as shown in FIG. 26 in accordance with an exemplary embodiment of the present invention.

FIG. 30 shows a specific size and construction material of the second unit 102 as shown in FIG. 26 (only the portion as shown in FIG. 13). In preferred embodiments of the invention, this part may be made of acrylonitrile butadiene styrene (ABS). The height of may be from 1 cm to 2 cm, and the width may be from 1 cm to 3 cm.

Figure 31A:
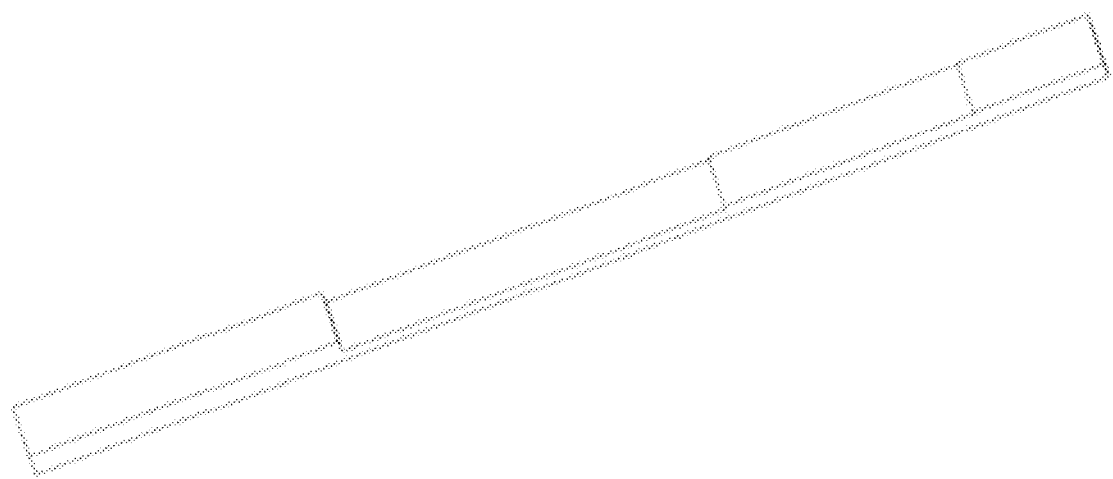
FIG. 31A illustrates a specific design of the chromatography medium (a "test strip") used in the "sample box" as shown in FIG. 26 in accordance with an exemplary embodiment of the present invention.
Figure 31B:
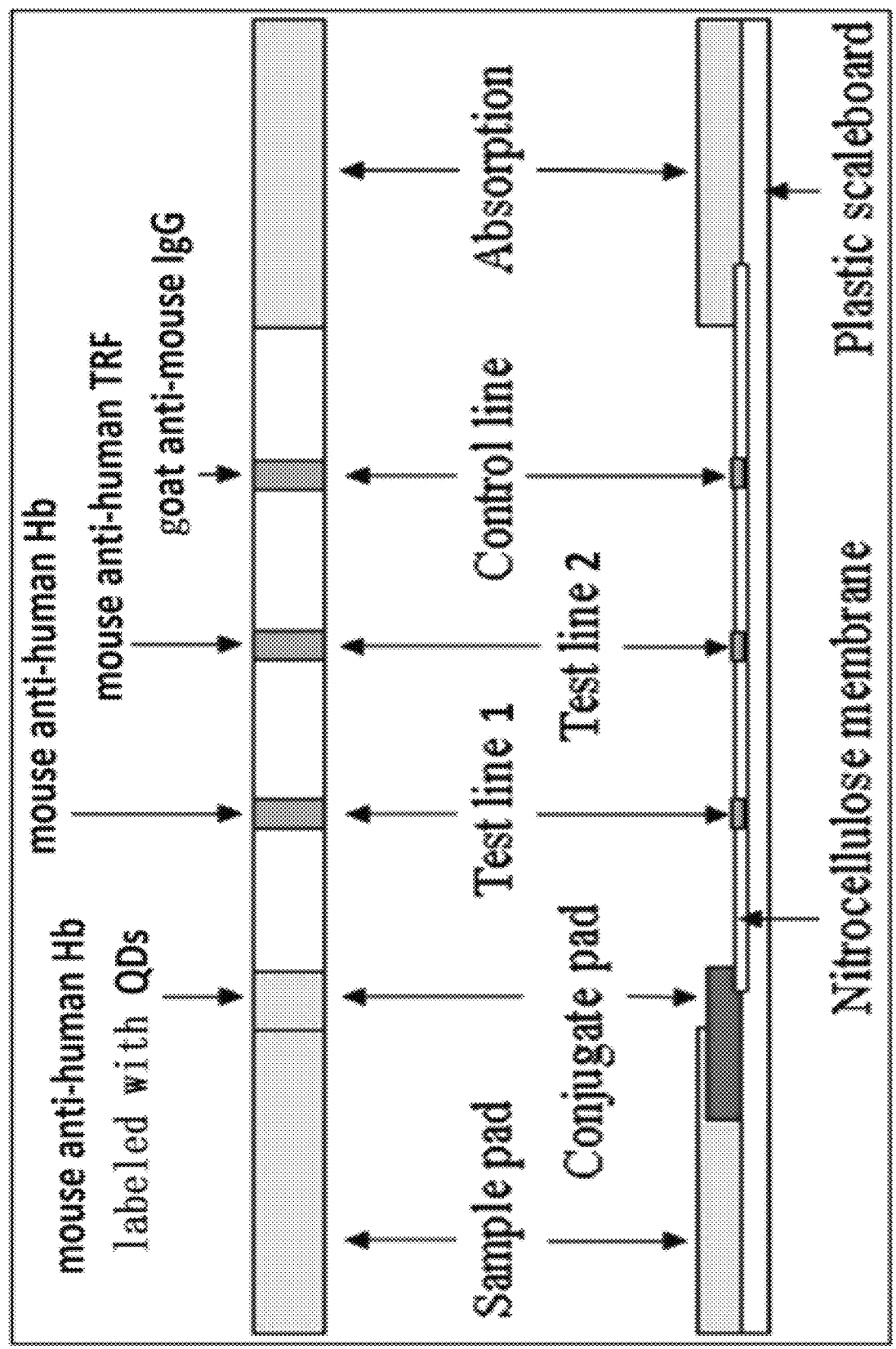
FIG. 31B shows a test strip with paired mouse anti-human hemoglobin monoclonal antibodies and paired mouse anti-human transferrin monoclonal antibodies in accordance with an exemplary embodiment of the present invention.
Figure 32:
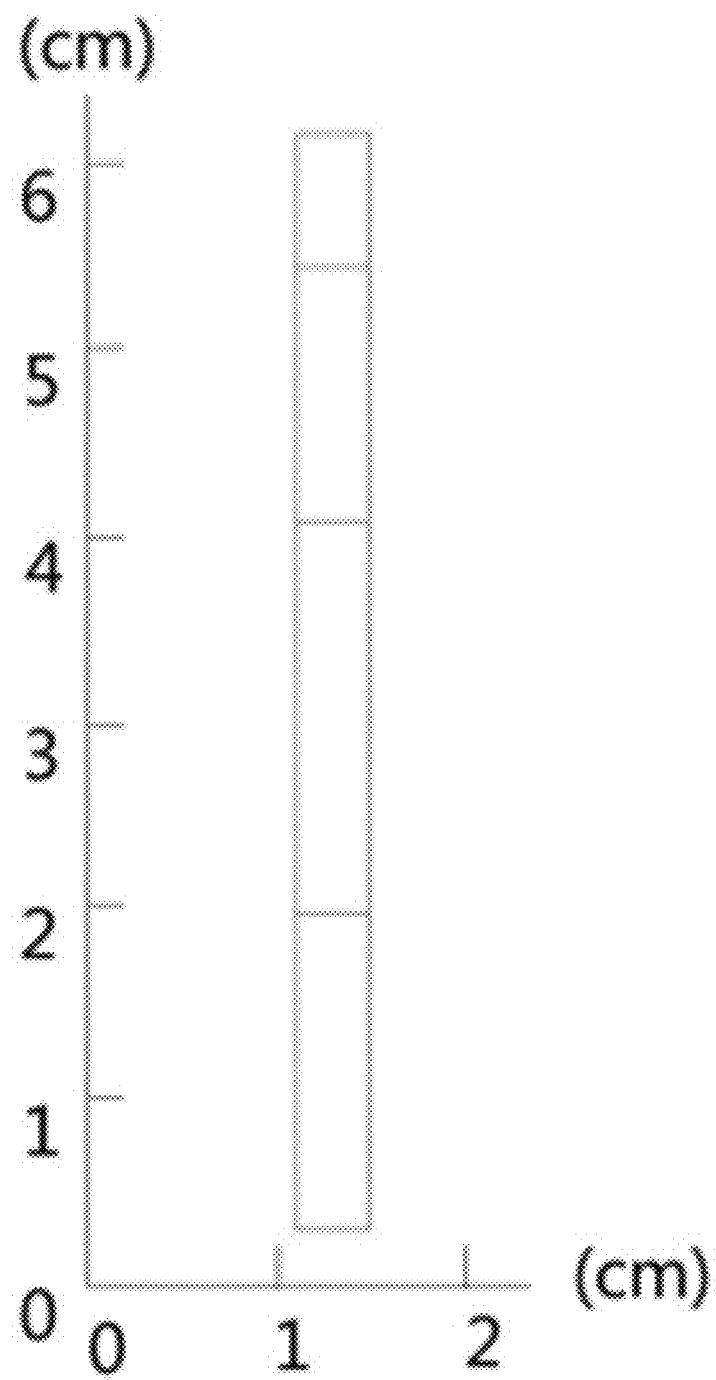
FIG. 32 indicates the specific size of a test trip in accordance with an exemplary embodiment of the present invention.

While FIG. 31A illustrates a specific design of the chromatography medium 104 (a "test strip") as shown in FIG. 26, FIG. 32 shows a specific size thereof, for example, a length of from 5 cm to 7 cm, and a width of from 0.1 cm to 0.7 cm. The testing strip can detect human fecal hemoglobin and transferrin quantitatively using a quantum dots based lateral flow immunochromatography method. In one embodiment as shown in FIG. 31B, the test strip may be prepared by paired mouse anti-human hemoglobin monoclonal antibodies and paired mouse anti-human transferrin monoclonal antibodies. In an example, the test strip 104 was prepared by paired mouse anti-human hemoglobin monoclonal antibodies. One of the paired antibodies was labeled with europium quantum dots (excitation: 365 nm; emission: 610 nm) and coated to a conjugate pad, and another one of the paired antibodies was coated onto nitrocellulose strip as test lines (test line 1 and test line 2). A goat anti-mouse IgG polyclonal antibody was coated onto nitrocellulose strip as a control line.

Figure 33:
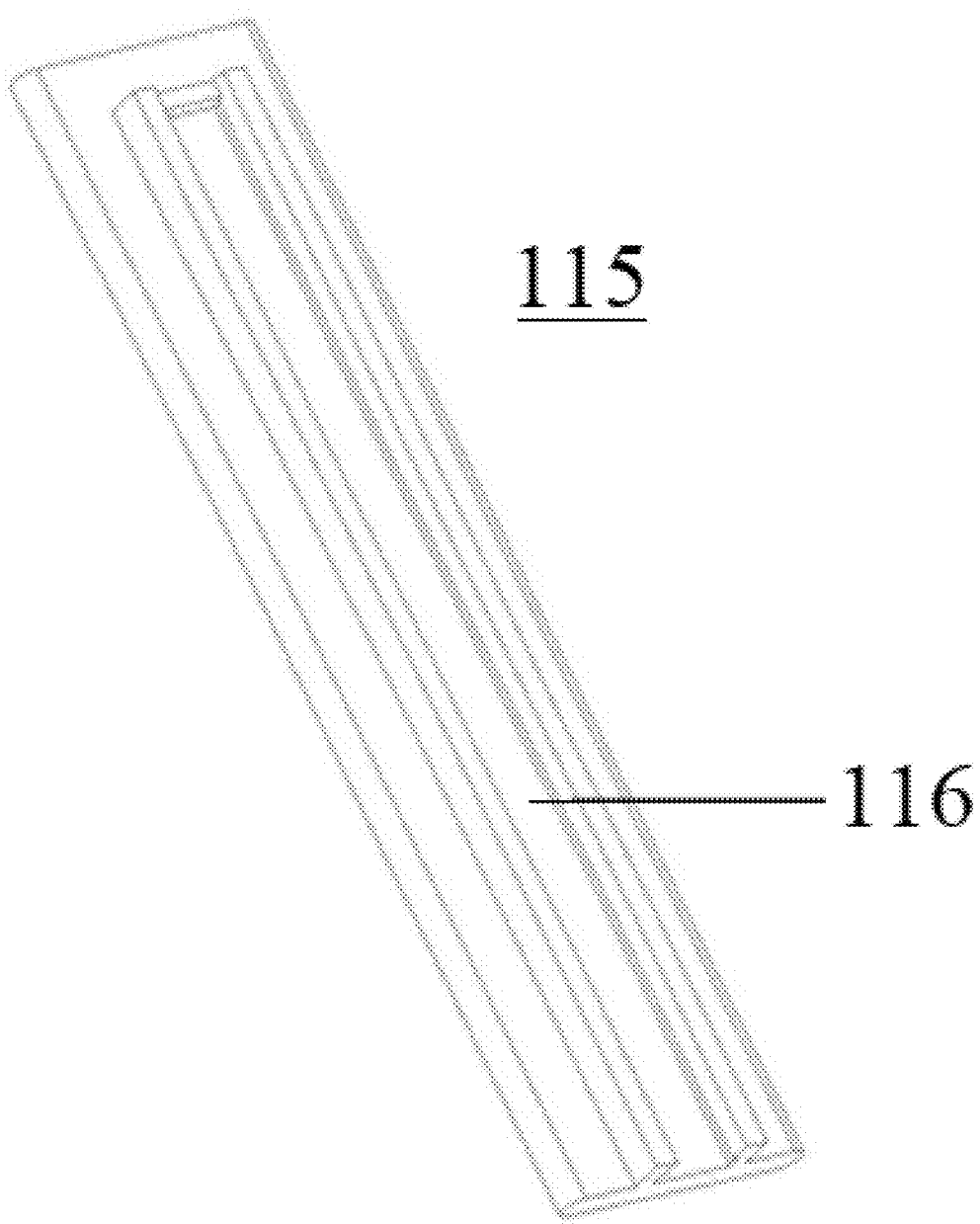
FIG. 33 demonstrates a holder for a test strip in accordance with an exemplary embodiment of the present invention.
Figure 34:
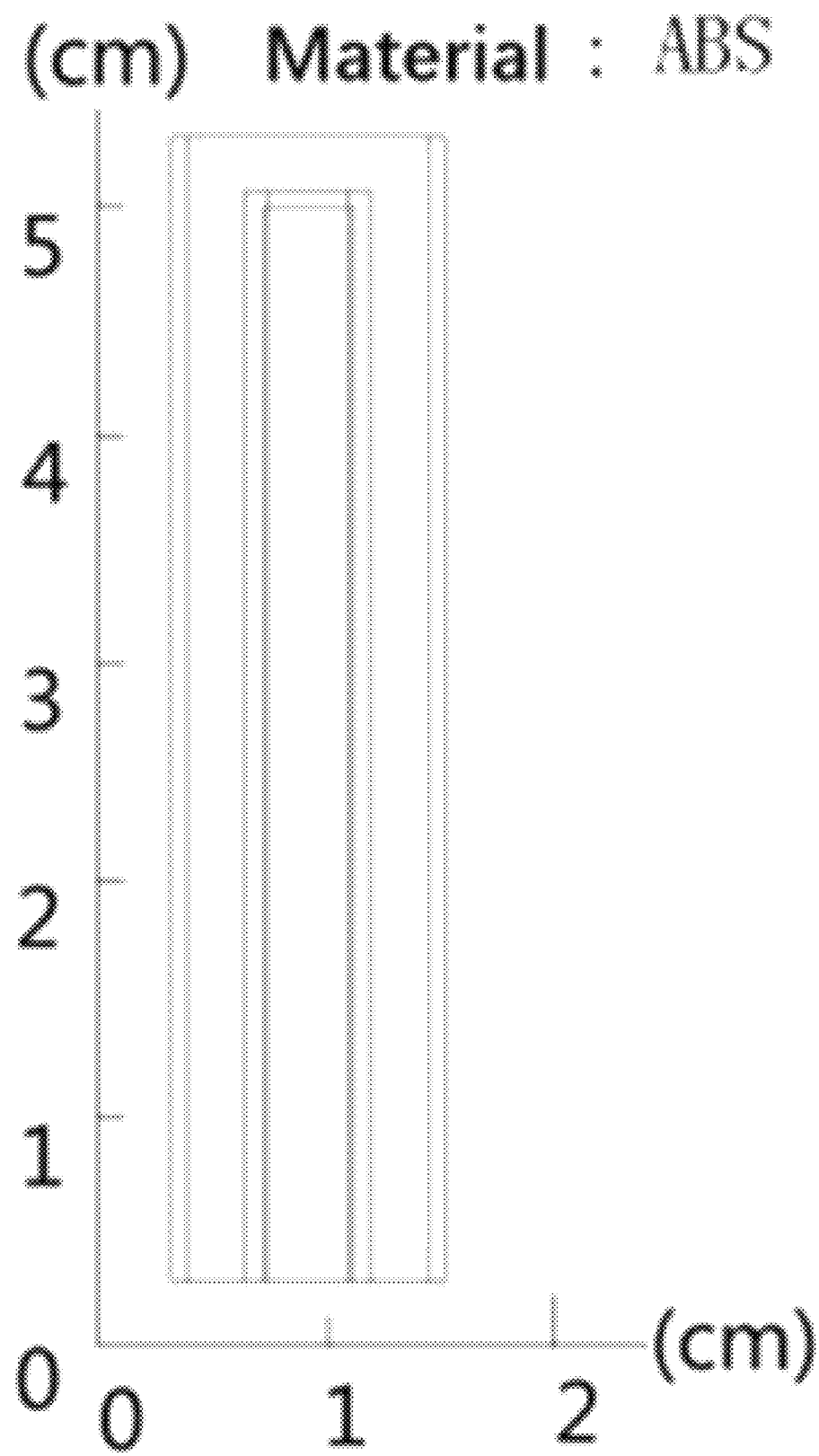
FIG. 34 indicates the specific size and construction material of a test strip holder in accordance with an exemplary embodiment of the present invention.

With reference to FIG. 33, a chromatography medium holder 115 may include a medium container 116 for housing and supporting the chromatography medium 104 as shown in FIG. 31A. FIG. 34 shows a specific size and construction material of the chromatography medium holder 115 as shown in FIG. 33 including its size and material of construction. In preferred embodiments of the invention, this part may be made of acrylonitrile butadiene styrene (ABS). The length of may be from 4 cm to 6 cm, and the width may be from 0.5 cm to 1.5 cm.

Figure 35:
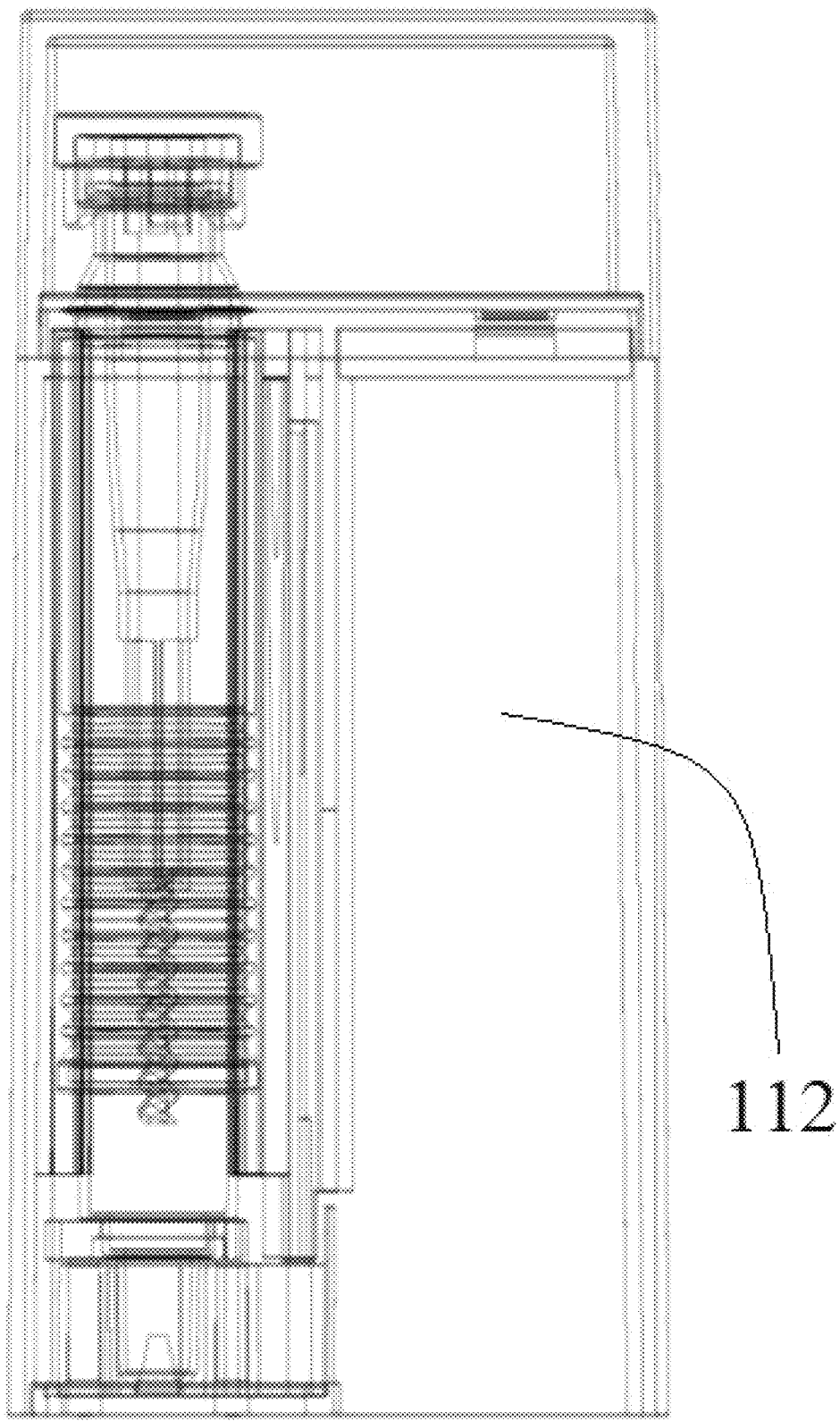
FIG. 35 depicts a specific "sample box" as completely assembled in accordance with an exemplary embodiment of the present invention.

FIG. 35 shows a specific embodiment of the second unit 102 as shown in FIG. 17 with the sample collection rod 5 loaded with a fecal sample is pushed into the mixing chamber 74 through the funnel 85. FIG. 35 may include the assembled components/parts as shown in FIGS. 20, 21, 22, 25, 29, 30, 32 and 34.

Figure 36:
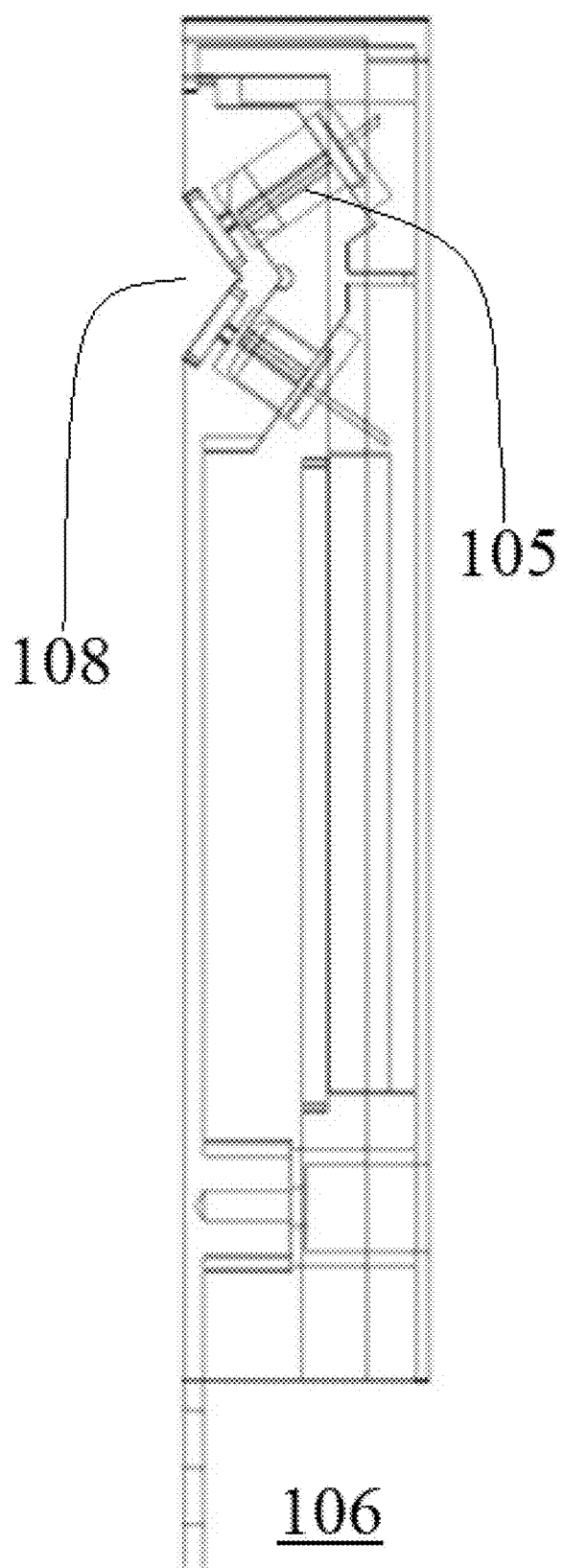
FIG. 36 shows a detector tower in the first unit as shown in FIG. 16 in accordance with an exemplary embodiment of the present invention.

FIG. 36 shows a specific embodiment of the tower 106 in the first unit 101 as shown in FIG. 16. The sharp top 107 of tower 106 is optional. Within the tower 106 is a detector 105 for detecting a signal (e.g. a stimulated signal) emitted from the chromatography medium 104 and through a detector window 108. The detector was designed with a photo probe to stretch into the sealed sample box and to detect the fluorescence signal on the test strip.

Figure 37:
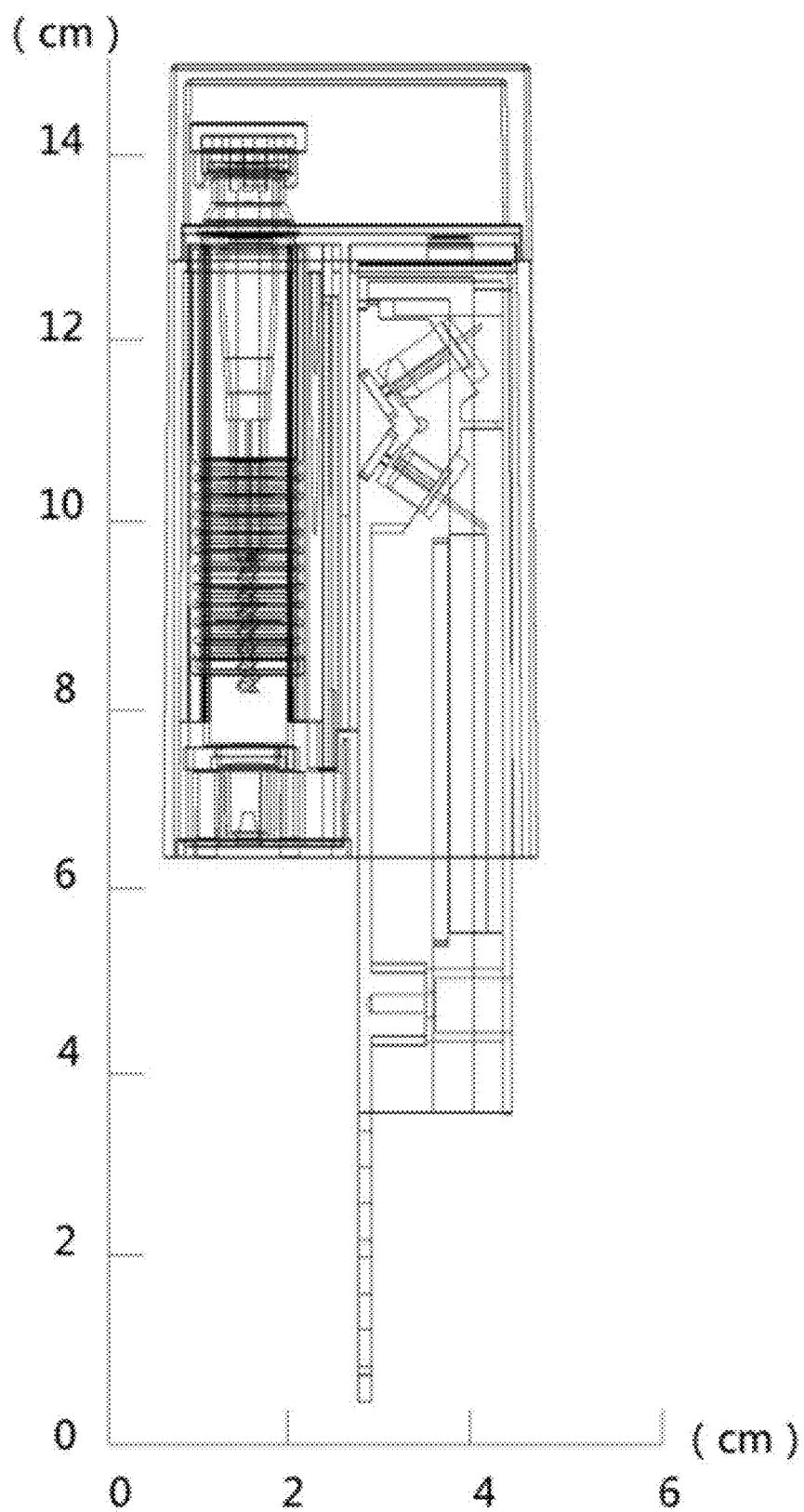
FIG. 37 indicates the specific size of the tower as shown in FIG. 36 inserted upward into a tower receptacle in "sample box" as shown in FIG. 35 in accordance with an exemplary embodiment of the present invention.

FIG. 37 shows that the tower 106 as shown in FIG. 36 is inserted upward into the tower receptacle 112 of the second unit 102 as shown in FIG. 35 with the sample collection rod 5, while the second unit 102 as shown in FIG. 35 is inserted downward into the harbor/slot 103 (not shown) of the first single unit 101.

Figure 38:
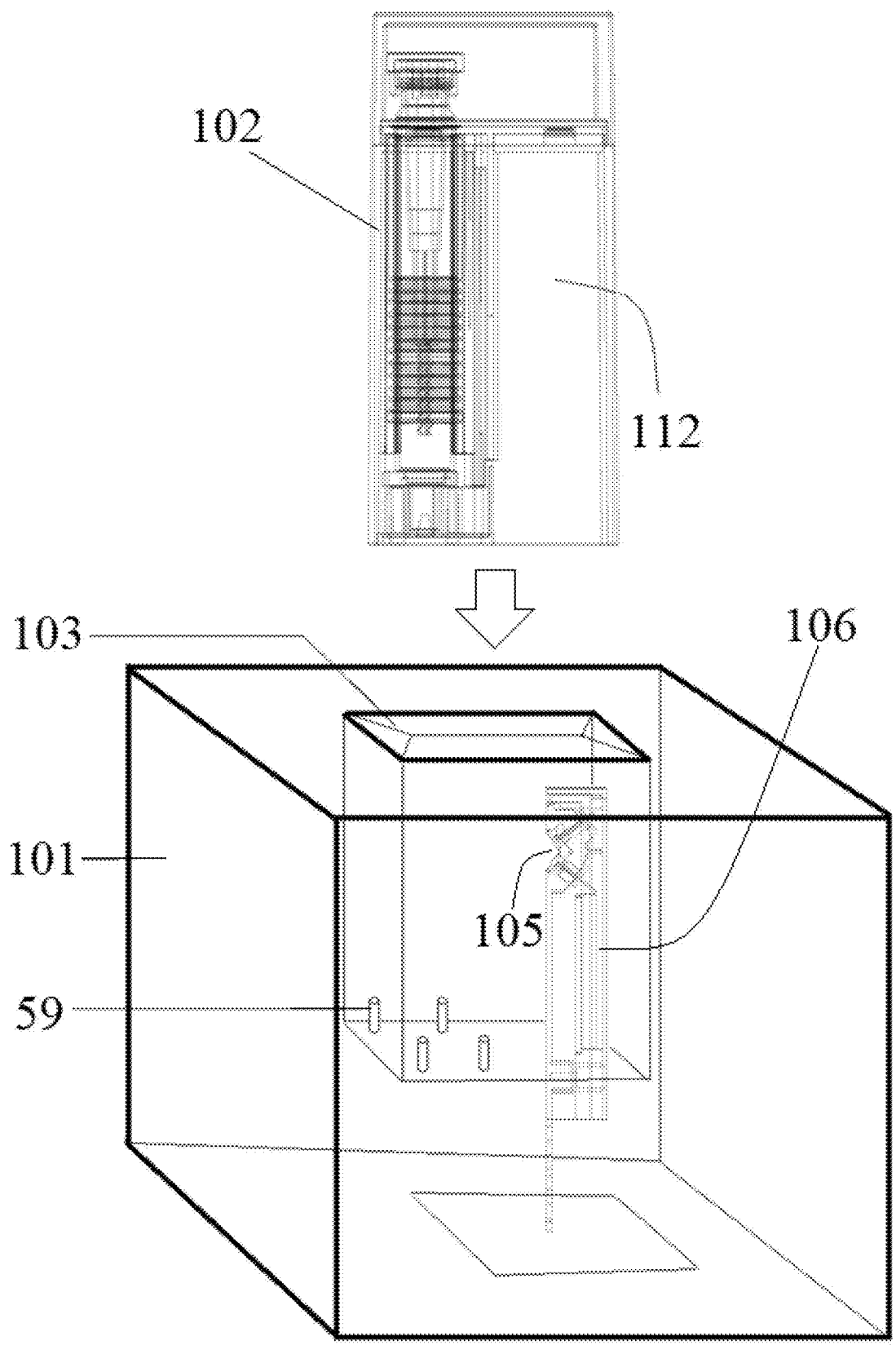
FIG. 38 illustrates a step of inserting a "sample box" into a first single unit in accordance with an exemplary embodiment of the present invention.

FIG. 38 shows that the second unit 102 as shown in FIG. 35 with the sample collection rod 5 is aligned with, and ready to be inserted downward into, the harbor/slot 103 of the first single unit 101, while the tower 106 of the first single unit 101 as shown in FIG. 36 is aligned with, and ready to be inserted upward into, the tower receptacle 112 of the second unit 102 as shown in FIG. 35.

In various exemplary embodiments, the analytical system of the invention may be used for screening colorectal cancer. The user can detect the presence of blood in the stools known as Fecal Occult Blood Test (FOBT). Immunological tests specific for human hemoglobin can also be performed with the analytical system of the invention. Immunoassay involves immunological reactions between the tumor marker, which is the antigen, and one or more specific binding partner(s), namely the antibodies directed against this antigen.

In an operation procedure, the user can (i) open the sample box 102 by removing the upper cap 109; (ii) collect fecal sample with fecal sample collection rod 5 by sticking it in to the fecal sample; (iii) put the fecal sample collection rod 5 into the sample box 102, and close the box by putting the upper cap 109 back on (the sample box is fully sealed after the sampling); (iv) open the detector box 101; (v) put the sample box 102 into the slot 103 next to the detector tower 106; and (vi) read the result from detector 105.

The test strip as shown in FIG. 31B was developed and verified to successfully detect the hemoglobin and transferrin. The detector 105 was verified by capturing the fluorescence signal on the test strip. The image processing software was also tested.

The test strip was installed in the sample box for test. The detector 105 can capture the fluorescence signals of the quantum dots (QD) on the test strip. The detector 105 is designed to have a UV light source of 365 nm and a CCD camera stretching into the sample box and to capture the image of the QD fluorescence on the test strip. Software with suitable algorithm is built in the system to process the image. The test strip was tested by human blood to have fluorescence signal under UV light. The detector 105 was tested to have the sensitivity of 1 ng/ml of hemoglobin. The detector 105 may be powered by a USB port, and equipped with integrated interface ports connecting to a computer, a smart phone, and the like. The test results can also be printed out directly.

Figure 40:
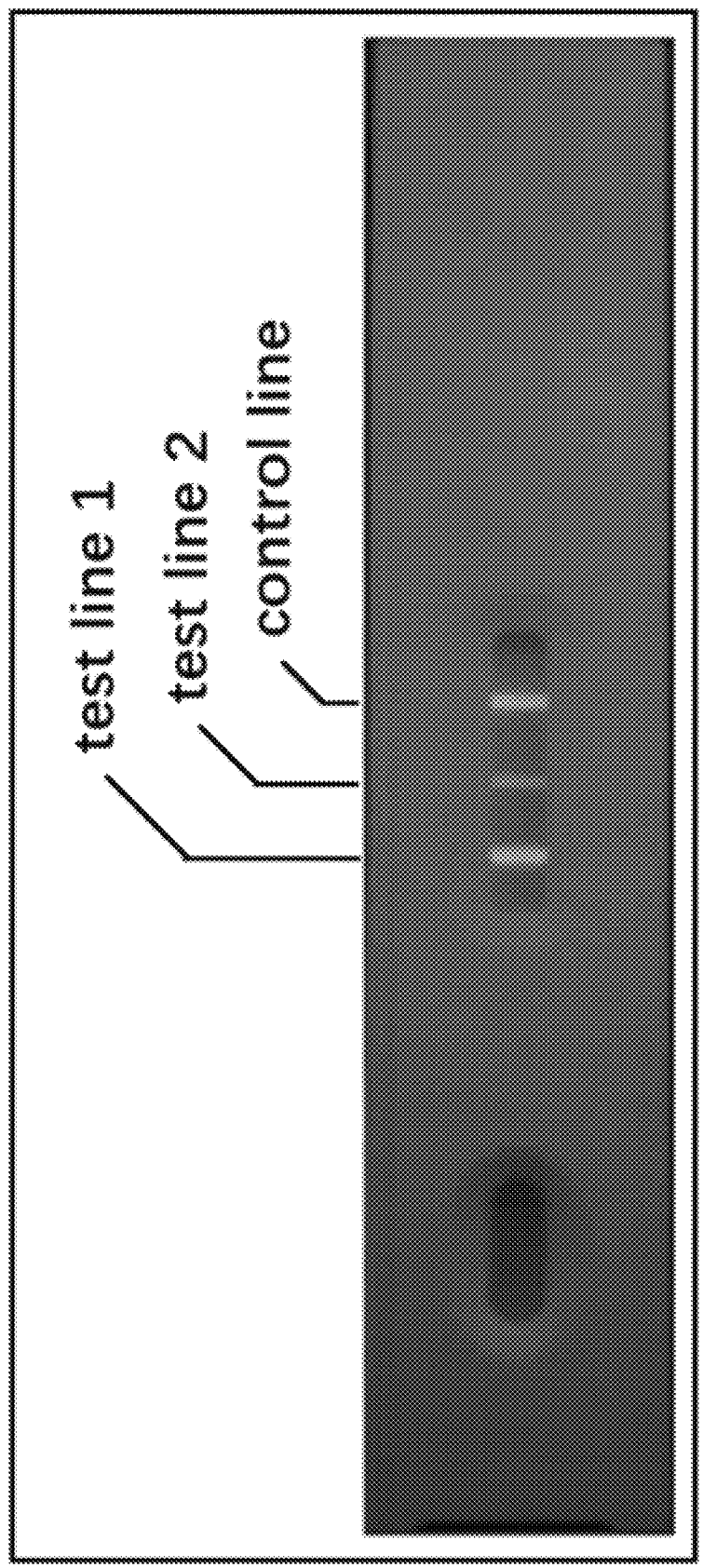
FIG. 40 shows visible florescent signals from a test strip under the irradiation of a UV light source (365 nm) in accordance with an exemplary embodiment of the present invention.

Regarding the test strip marked quantum dots, sample flow passes by the conjugate pad first, and the hemoglobin or transferrin will bind to the first paired antibody (labeled with europium quantum dots). The sample continues to move to the test lines 1 and 2, and the hemoglobin or transferrin will bind to the second paired antibody coated at test lines 1 and 2 and then detached with QDs. Extra QD labeled antibodies continue to go to the control line and detached by anti-mouse IgG antibody there. Under the irradiation of a UV light source (365 nm), the signal can be seen on the test strip, as shown in FIG. 40.

Figure 41:
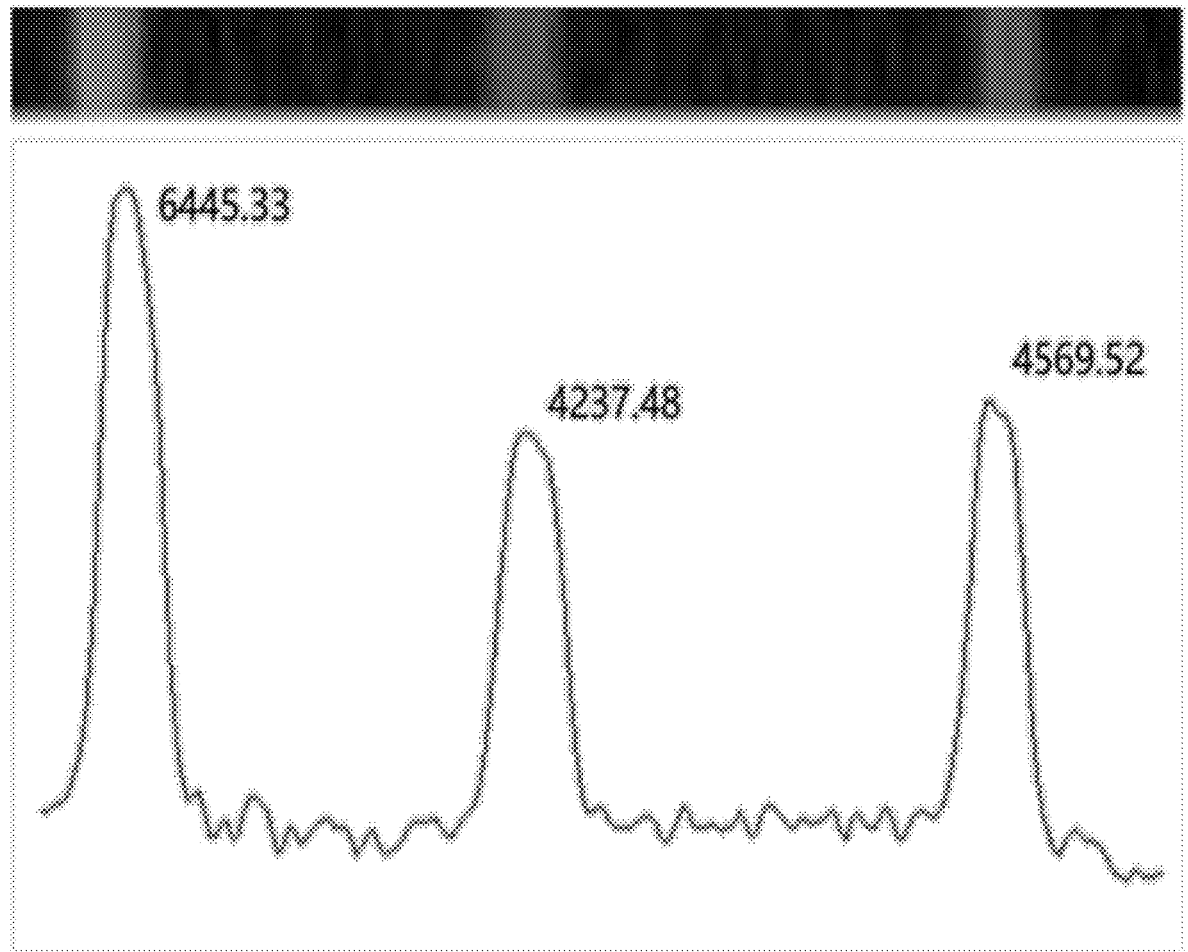
FIG. 41 shows recorded fluorescence intensity of quantum dots (QD) on a test strip in accordance with an exemplary embodiment of the present invention.

A UV light emitting diode was used to illuminate the QDs, and a CCD was used to capture the image, using image-processing software to analyze the intensity of the signal at the test lines and the control line. The intensity of the signal is recorded with the fluorescence of the QDs, as shown in FIG. 41. The detector was demonstrated to have the sensitivity of 1 nanogram/ml of human hemoglobin, which is comparable to conventional lab equipped detectors.

Gradiently diluted human hemoglobin was used as standard, and it was added to the sample box. The sample box is then inserted into the detector system to test. The result is shown in the following Table.

| Standard (ng/ml) | Detector Reading (T/C) |
| --- | --- |
| 0 | 0 |
| 8 | 0.01 |
| 16 | 0.02 |
| 32 | 0.03 |
| 64 | 0.08 |
| 128 | 0.12 |
| 256 | 0.3 |
| 512 | 0.49 |
| 1024 | 0.89 |

Figure 39:
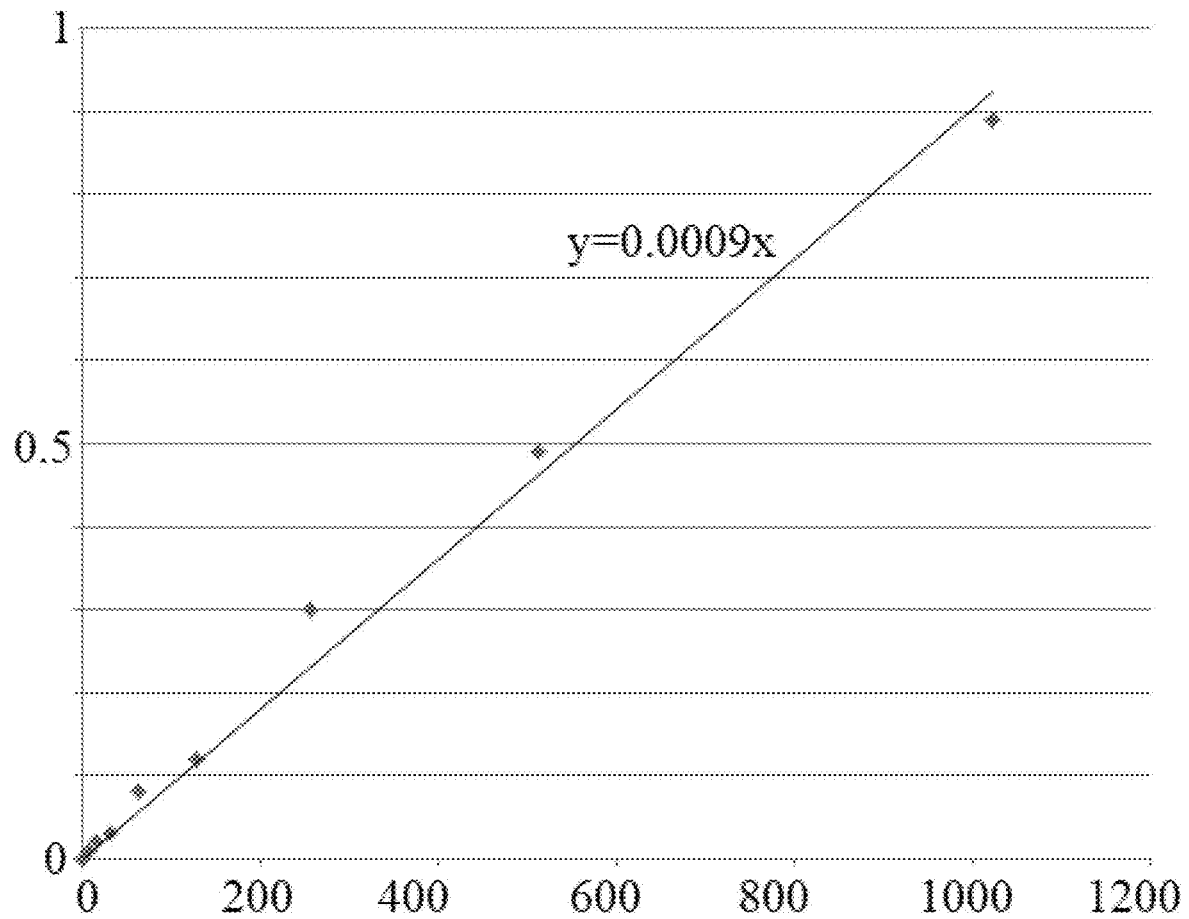
FIG. 39 is standard curve for hemoglobin concentration in accordance with an exemplary embodiment of the present invention.

The standard curve is shown in FIG. 39, in which x=hemoglobin concentration, y=T/C (T is test line reading, and C is control line reading).

Human fecal samples were added to the sample box, and then the sample box was put into the detector to obtain the test results as shown below:

| Sample # | T/C | Hemoglobin Concentration (ng/ml) |
|---|---|---|
| 1 | 0.009 | 10.00 |
| 2 | 0.005 | 5.22 |
| 3 | 0.035 | 39.33 |
| 4 | 0.029 | 31.89 |
| 5 | 1.309 | 1454.56 |
| 6 | 0.707 | 785.56 |
| 7 | 0.004 | 4.22 |
| 8 | 0.000 | 0.00 |
| 9 | 0.005 | 5.33 |
| 10 | 0.065 | 71.67 |
| 11 | 0.054 | 60.33 |
| 12 | 0.062 | 68.67 |

Sample detection card 104 preparation: using europium quantum dots (excitation: 365 nm; emission: 610 nm) lateral flow immunochromatography method to detect fecal human hemoglobin. Paired mouse anti-human hemoglobin (Hb) monoclonal antibodies were used, one of them is labeled with europium quantum dots to be mixing with diluted fecal sample and another one is to be coated onto immunochromatography medium. Detector probe parameter: light source 365 nm LED, receiver 610 nm photodiode. Fecal samples: fecal samples were donated by 10 colorectal cancer patients and 10 normal persons. The results are shown in the table below:

| Colorectal cancer patients | Fecal hemoglobin concentration (ng/ml) | Normal persons | Fecal hemoglobin concentration (ng/ml) |
|---|---|---|---|
| 1 | 1128 | 1 | 42 |
| 2 | 2568 | 2 | 0 |
| 3 | 443 | 3 | 63 |
| 4 | 11311 | 4 | 47 |
| 5 | 6916 | 5 | 103 |
| 6 | 1220 | 6 | 63 |
| 7 | 603 | 7 | 163 |
| 8 | 1304 | 8 | 387 |
| 9 | 850 | 9 | 26 |
| 10 | 4043 | 10 | 0 |

Some operations, tasks, and functions of the analytical method of the invention may be computer-executed, computerized, processor-executed, software-implemented, or computer-implemented. It may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices. The present application may be implemented by means of software plus necessary hardware platforms, or of course, may also be implemented all by software or hardware.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. An analytical system comprising a sample collection module, a sample management module, and a sample analysis module;
   wherein the sample management module comprises:
   a mixing chamber for receiving an amount of sample from the sample collection module and mixing the received sample with a liquid to formulate a sample preparation, wherein the mixing chamber includes an outlet opening for releasing the sample preparation from the mixing chamber;
   a sample tray below the mixing chamber, the sample tray having a raised and enclosed rim to define a receptacle area for receiving an amount of the sample preparation released from the mixing chamber, wherein an island is protruded out from the receptacle area, and the island engages with the outlet opening of the mixing chamber and seals the outlet opening to prevent releasing of the sample preparation through it; and
   a pressure delivery assembly comprising a lower member below the sample tray and an upper member above the sample tray for contacting against the mixing chamber, wherein the lower member is contactable to the upper member, and a force from the lower member can be exerted up against the upper member which transmits the force along against the mixing chamber so as to squeeze and deform the mixing chamber, reduce a volume thereof, and in the meanwhile, disengage the outlet opening from the island to unseal the outlet opening, and release an amount of the sample preparation from the mixing chamber into the receptacle area;
   wherein the pressure delivery assembly (80) further comprises an alignment channel (83) to align the lower member's (81) movement and the upper member's (82) movement before the two members (81) and (82) meet and contact each other; and
   wherein said sample preparation released into the receptacle area is delivered to the sample analysis module.

2. The analytical system according to claim 1, wherein the sample tray (76) and the alignment channel (83) are integrated to each other.

3. The analytical system according to claim 1, wherein the upper member comprises a contacting portion contactable against the mixing chamber, and one, two, three, four or more downward legs extended downwardly from the contacting portion.

4. The analytical system according to claim 3, wherein the lower member comprises a same number of upward leg(s) as the downward leg(s), and the upward leg(s) is (are) contactable to the downward leg(s).

5. The analytical system according to claim 4, wherein the pressure delivery assembly (80) further comprises a same number of alignment channel(s) (83) as the upward or downward leg(s), to align movement of the upward leg(s) and movement of the downward leg(s), before the upward leg(s) and the downward leg(s) meet and contact each other within the alignment channel(s).

6. The analytical system according to claim 5, wherein the sample tray and the alignment channel(s) (83) are integrated to each other.

7. The analytical system according to claim 6, wherein the alignment channel(s) (83) may go through the receptacle area (78) and/or an area of the sample tray (76) other than the receptacle area (78).

8. The analytical system according to claim 1, wherein the upper member comprises a table with 3 or 4 downward legs and a hole on tabletop, wherein the outlet opening of the mixing chamber is inserted through the hole, and located below the tabletop, and the tabletop is contactable to the mixing chamber.

9. The analytical system according to claim 8, wherein the lower member comprises a same number of upward legs as the downward legs, and wherein the pressure delivery assembly further comprises a same number of alignment channels as the upward or downward legs, to align movement of the upward legs and movement of the downward legs, before the upward legs and the downward legs meet and contact each other within the alignment channels.

10. The analytical system according to claim 1, wherein the sample collection module includes a sample collection rod with spiral grooves that can be filled or loaded with a sample.

11. The analytical system according to claim 10, wherein the sample management module (72) includes a sample funnel for the sample collection rod loaded with a collected sample to go through within.

12. The analytical system according to claim 11, wherein the funnel has a top opening and a bottom opening that is smaller than the top opening, and wherein an internal diameter of the bottom opening is not bigger than an external diameter of the sample collection rod, and is so configured that, when the sample collection rod goes through the bottom opening, all the sample collected on the sample collection rod except the sample within the spiral grooves are wiped off from the rod, and are prevented from mixing with the liquid to formulate the sample preparation (84).

13. The analytical system according to claim 12, wherein the funnel further comprises one, two or more fingers extended from a peripheral of the bottom opening, and tip(s) of the one, two or more fingers is (are) configured to contact the sample collection rod and to remove the sample within the spiral grooves from the sample collection rod when the rod is moving downward.

14. The analytical system according to claim 13, wherein the tip(s) of the one, two or more fingers is (are) bended inwardly.

15. The analytical system according to claim 12, wherein the sample collection rod comprises a locking cap configured to lock and seal the top opening of the funnel, after the sample collection rod is inserted all the way into the funnel and the mixing chamber.

16. The analytical system according to claim 1, wherein the sample analysis module and the lower member of the pressure delivery assembly are built into a first single unit; wherein the mixing chamber, the sample tray and the upper member of the pressure delivery assembly are built into a second single unit; and wherein the first single unit includes a harbor for receiving the second single unit.

17. The analytical system according to claim 16, wherein the second single unit includes one or more alignment channels to align the lower member's movement and the upper member's movement before the two members meet and contact each other; and wherein said one or more alignment channels are integrated with the sample tray, and wherein said one or more alignment channels are so configured that the sample preparation (84) in the receptacle area cannot flow into said one or more alignment channels.

18. The analytical system according to claim 17, wherein the second single unit includes a chromatography medium with antibody extending from the receptacle area and absorbing the sample preparation (84) therein; and wherein the first single unit includes a detector for detecting a signal from the chromatography medium after it absorbs the sample preparation (84).

19. An analytical method of using the analytical system according to claim 1, comprising
  (1) collecting a sample with the sample collection module;
  (2) aliquoting the sample and mixing the aliquoted sample with a liquid to formulate a sample preparation in the mixing chamber;
  (3) applying a force up against the upper member with the lower member and transmitting the force against the mixing chamber;
  (4) squeezing and deforming the mixing chamber to reduce a volume thereof, and simultaneously disengaging the outlet opening from the island to unseal the outlet opening;
  (5) releasing an amount of the sample preparation from the mixing chamber into the receptacle area; and
  (6) analyzing the released sample preparation with the sample analysis module.

20. The analytical method of claim 19, which is used for diagnosing colorectal cancer, wherein the sample comprises a fecal sample.

* * * * *